US012594143B2

(12) United States Patent
Mason et al.

(10) Patent No.: US 12,594,143 B2
(45) Date of Patent: Apr. 7, 2026

(54) METHOD FOR TRACKING, PREDICTING, AND PROACTIVELY CORRECTING MALOCCLUSION AND RELATED ISSUES

(71) Applicant: Align Technology, Inc., San Jose, CA (US)

(72) Inventors: David Mason, Morgan Hill, CA (US); Douglas Brandt, San Pablo (CR)

(73) Assignee: ALIGN TECHNOLOGY, INC., San Jose, CA (US)

( * ) Notice: Subject to any disclaimer, the term of this patent is extended or adjusted under 35 U.S.C. 154(b) by 385 days.

(21) Appl. No.: 17/492,306

(22) Filed: Oct. 1, 2021

(65) Prior Publication Data
US 2022/0015868 A1     Jan. 20, 2022

Related U.S. Application Data

(63) Continuation of application No. 14/804,153, filed on Jul. 20, 2015, now Pat. No. 11,147,652.

(60) Provisional application No. 62/079,451, filed on Nov. 13, 2014.

(51) Int. Cl.
*A61C 7/00*       (2006.01)
*A61C 7/08*       (2006.01)
*G16H 50/50*      (2018.01)
*G16Z 99/00*      (2019.01)
(52) U.S. Cl.
CPC ............... *A61C 7/002* (2013.01); *A61C 7/08* (2013.01); *G16H 50/50* (2018.01); *G16Z 99/00* (2019.02)

(58) Field of Classification Search
CPC .. A61C 7/002; A61C 7/08; A61C 7/00; A61C 9/0053; G16H 50/50; G16H 50/00; G16Z 99/00; G06F 19/00; G06F 19/45; A61B 5/682; A61B 5/4542; A61B 5/4547; A61B 5/4552; A61B 5/4557; A61B 5/103; A61B 5/111; A61D 5/00
USPC ........................................................ 703/2
See application file for complete search history.

(56) References Cited

U.S. PATENT DOCUMENTS

| | | | |
|---|---|---|---|
| 6,227,850 B1 | 5/2001 | Chishti et al. | |
| 6,227,851 B1 | 5/2001 | Chishti et al. | |
| 6,299,440 B1 | 10/2001 | Phan et al. | |
| 6,315,553 B1 * | 11/2001 | Sachdeva ................. A61C 3/00 | |
| | | | 433/213 |
| 6,318,994 B1 | 11/2001 | Chishti et al. | |
| 6,371,761 B1 | 4/2002 | Cheang et al. | |

(Continued)

FOREIGN PATENT DOCUMENTS

| | | |
|---|---|---|
| JP | 2003233671 A | 8/2003 |
| JP | 2012045247 A | 3/2012 |

*Primary Examiner* — Eric J Rosen
*Assistant Examiner* — Mirayda A Aponte
(74) *Attorney, Agent, or Firm* — Wilson Sonsini Goodrich & Rosati

(57)                     ABSTRACT

Methods and systems for predicting a future dental or orthodontic condition(s) are provided. In one aspect, a computer-implemented method for calculating a future position of an intraoral object of a patient's intraoral cavity is provided. The method can include receiving first and second digital data representative of an actual state of the intraoral cavity at first and second time points, evaluating a characteristic of an intraoral object based on the first and second digital data, predicting a future condition of the intraoral object at a third time point, and determining a treatment option to treat the future condition.

22 Claims, 19 Drawing Sheets

(56) References Cited

U.S. PATENT DOCUMENTS

| | | | |
|---|---|---|---|
| 6,386,878 B1 | 5/2002 | Pavlovskaia et al. |
| 6,406,292 B1 | 6/2002 | Chishti et al. |
| 6,409,504 B1 | 6/2002 | Jones et al. |
| 6,457,972 B1 | 10/2002 | Chishti et al. |
| 6,488,499 B1 | 12/2002 | Miller |
| 6,514,074 B1 | 2/2003 | Chishti et al. |
| 6,621,491 B1 | 9/2003 | Baumrind et al. |
| 6,688,886 B2 | 2/2004 | Hughes et al. |
| 6,726,478 B1 | 4/2004 | Isiderio et al. |
| 6,739,869 B1 | 5/2004 | Taub et al. |
| 6,767,208 B2 | 7/2004 | Kaza |
| 6,783,360 B2 | 8/2004 | Chishti |
| 7,040,896 B2 | 5/2006 | Pavlovskaia et al. |
| 7,063,532 B1 | 6/2006 | Jones et al. |
| 7,074,038 B1 | 7/2006 | Miller |
| 7,074,039 B2 | 7/2006 | Kopelman et al. |
| 7,108,508 B2 | 9/2006 | Hedge et al. |
| 7,134,874 B2 | 11/2006 | Chishti et al. |
| 7,160,107 B2 | 1/2007 | Kopelman et al. |
| 7,241,142 B2 | 7/2007 | Abolfathi et al. |
| 7,309,230 B2 | 12/2007 | Wen |
| 7,357,634 B2 | 4/2008 | Knopp |
| 7,555,403 B2 | 6/2009 | Kopelman et al. |
| 7,637,740 B2 | 12/2009 | Knopp |
| 7,689,398 B2 | 3/2010 | Cheng et al. |
| 7,736,147 B2 | 6/2010 | Kaza et al. |
| 7,746,339 B2 | 6/2010 | Matov et al. |
| 7,844,356 B2 | 11/2010 | Matov et al. |
| 7,844,429 B2 | 11/2010 | Matov et al. |
| 7,865,259 B2 | 1/2011 | Kuo et al. |
| 7,878,804 B2 | 2/2011 | Korytov et al. |
| 7,880,751 B2 | 2/2011 | Kuo et al. |
| 7,904,308 B2 | 3/2011 | Arnone et al. |
| 7,930,189 B2 | 4/2011 | Kuo |
| 7,970,627 B2 | 6/2011 | Kuo et al. |
| 8,044,954 B2 | 10/2011 | Kitching et al. |
| 8,092,215 B2 | 1/2012 | Stone-Collonge et al. |
| 8,099,268 B2 | 1/2012 | Kitching et al. |
| 8,108,189 B2 | 1/2012 | Chelnokov et al. |
| 8,260,591 B2 | 9/2012 | Kass et al. |
| 8,275,180 B2 | 9/2012 | Kuo |
| 8,401,826 B2 | 3/2013 | Cheng et al. |
| 8,439,672 B2 | 5/2013 | Matov et al. |
| 8,788,285 B2 | 7/2014 | Kuo |
| 8,843,381 B2 | 9/2014 | Kuo et al. |
| 8,896,592 B2 | 11/2014 | Boltunov et al. |
| 8,930,219 B2 | 1/2015 | Trosien et al. |
| 9,037,439 B2 | 5/2015 | Kuo et al. |
| 9,060,829 B2 | 6/2015 | Sterental et al. |
| 9,125,709 B2 | 9/2015 | Matty |
| 9,211,166 B2 | 12/2015 | Kuo et al. |
| 9,364,296 B2 | 6/2016 | Kuo |
| 9,414,897 B2 | 8/2016 | Wu et al. |
| 9,492,245 B2 | 11/2016 | Sherwood et al. |
| 9,642,678 B2 | 5/2017 | Kuo |
| 10,248,883 B2 | 4/2019 | Borovinskih et al. |
| 10,342,638 B2 | 7/2019 | Kitching et al. |
| 10,463,452 B2 | 11/2019 | Matov et al. |
| 10,595,966 B2 | 3/2020 | Carrier, Jr. et al. |
| 10,617,489 B2 | 4/2020 | Grove et al. |
| 10,722,328 B2 | 7/2020 | Velazquez et al. |
| 10,758,322 B2 | 9/2020 | Pokotilov et al. |
| 10,779,718 B2 | 9/2020 | Meyer et al. |
| 10,792,127 B2 | 10/2020 | Kopelman et al. |
| 10,828,130 B2 | 11/2020 | Pokotilov et al. |
| 10,835,349 B2 | 11/2020 | Cramer et al. |
| 10,973,611 B2 | 4/2021 | Pokotilov et al. |
| 10,996,813 B2 | 5/2021 | Makarenkova et al. |
| 10,997,727 B2 | 5/2021 | Xue et al. |
| 11,020,205 B2 | 6/2021 | Li et al. |
| 11,020,206 B2 | 6/2021 | Shi et al. |
| 11,026,766 B2 | 6/2021 | Chekh et al. |
| 11,033,359 B2 | 6/2021 | Velazquez et al. |
| 11,071,608 B2 | 7/2021 | Derakhshan et al. |
| 11,096,763 B2 | 8/2021 | Akopov et al. |
| 11,116,605 B2 | 9/2021 | Nyukhtikov et al. |
| 11,147,652 B2 * | 10/2021 | Mason .................... G16Z 99/00 |
| 11,151,753 B2 | 10/2021 | Gao et al. |
| 11,259,896 B2 | 3/2022 | Matov et al. |
| 2003/0008259 A1 | 1/2003 | Kuo et al. |
| 2003/0143509 A1 | 7/2003 | Kopelman et al. |
| 2003/0207227 A1 | 11/2003 | Abolfathi |
| 2004/0137400 A1 | 7/2004 | Chishti et al. |
| 2004/0152036 A1 | 8/2004 | Abolfathi |
| 2004/0197728 A1 | 10/2004 | Abolfathi et al. |
| 2004/0259049 A1 | 12/2004 | Kopelman et al. |
| 2005/0182654 A1 | 8/2005 | Abolfathi et al. |
| 2005/0244791 A1 | 11/2005 | Davis et al. |
| 2006/0127852 A1 | 6/2006 | Wen |
| 2006/0127854 A1 | 6/2006 | Wen |
| 2006/0275731 A1 | 12/2006 | Wen et al. |
| 2006/0275736 A1 | 12/2006 | Wen et al. |
| 2008/0306724 A1 * | 12/2008 | Kitching .................. A61C 7/00 704/2 |
| 2010/0009308 A1 * | 1/2010 | Wen ......................... A61C 7/08 700/118 |
| 2010/0068672 A1 | 3/2010 | Arjomand et al. |
| 2010/0068676 A1 | 3/2010 | Mason et al. |
| 2010/0092907 A1 | 4/2010 | Knopp |
| 2010/0145664 A1 | 6/2010 | Hultgren et al. |
| 2010/0167243 A1 | 7/2010 | Spiridonov et al. |
| 2010/0280798 A1 * | 11/2010 | Pattijn .................... A61C 7/002 703/1 |
| 2013/0204599 A1 | 8/2013 | Matov et al. |
| 2016/0310235 A1 | 10/2016 | Derakhshan et al. |
| 2017/0273760 A1 | 9/2017 | Morton et al. |
| 2018/0280118 A1 | 10/2018 | Cramer |
| 2019/0029784 A1 | 1/2019 | Moalem et al. |
| 2019/0053876 A1 | 2/2019 | Sterental et al. |
| 2019/0192259 A1 | 6/2019 | Kopelman et al. |
| 2019/0328487 A1 | 10/2019 | Levin et al. |
| 2019/0328488 A1 | 10/2019 | Levin et al. |
| 2019/0333622 A1 | 10/2019 | Levin et al. |
| 2019/0343601 A1 | 11/2019 | Roschin et al. |
| 2020/0000552 A1 | 1/2020 | Mednikov et al. |
| 2020/0000554 A1 | 1/2020 | Makarenkova et al. |
| 2020/0000555 A1 | 1/2020 | Yuryev et al. |
| 2020/0085546 A1 | 3/2020 | Li et al. |
| 2020/0107915 A1 | 4/2020 | Roschin et al. |
| 2020/0155274 A1 | 5/2020 | Pimenov et al. |
| 2020/0214800 A1 | 7/2020 | Matov et al. |
| 2020/0297458 A1 | 9/2020 | Roschin et al. |
| 2020/0306011 A1 | 10/2020 | Chekhonin et al. |
| 2020/0306012 A1 | 10/2020 | Roschin et al. |
| 2020/0315744 A1 | 10/2020 | Cramer |
| 2020/0360109 A1 | 11/2020 | Gao et al. |
| 2021/0073998 A1 | 3/2021 | Brown et al. |
| 2021/0134436 A1 | 5/2021 | Meyer et al. |
| 2021/0174477 A1 | 6/2021 | Shi et al. |

* cited by examiner

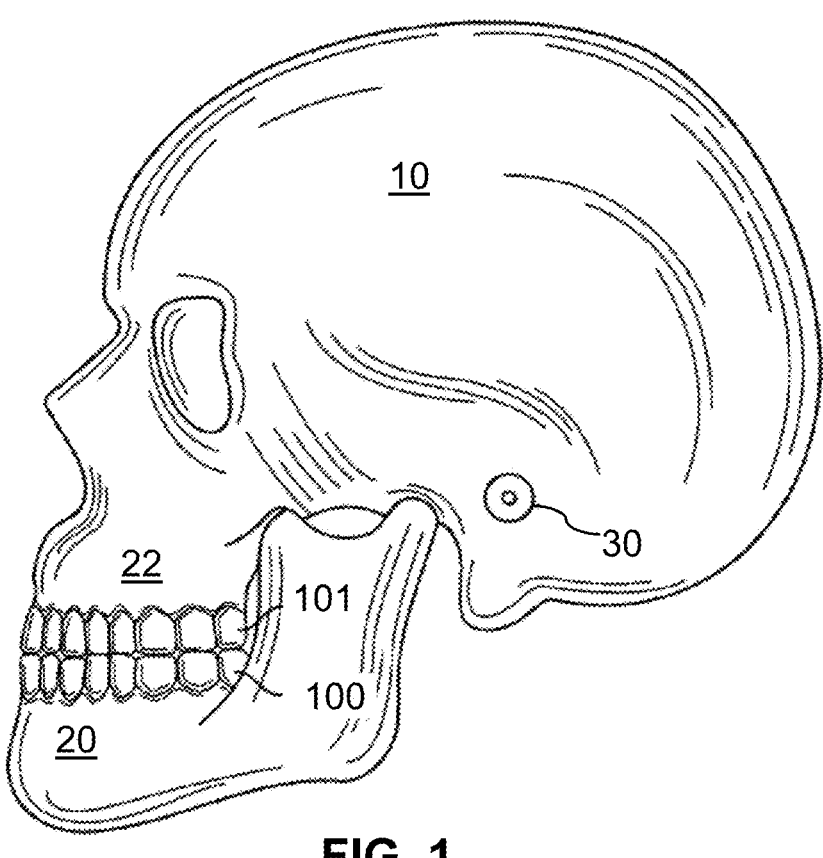
FIG. 1
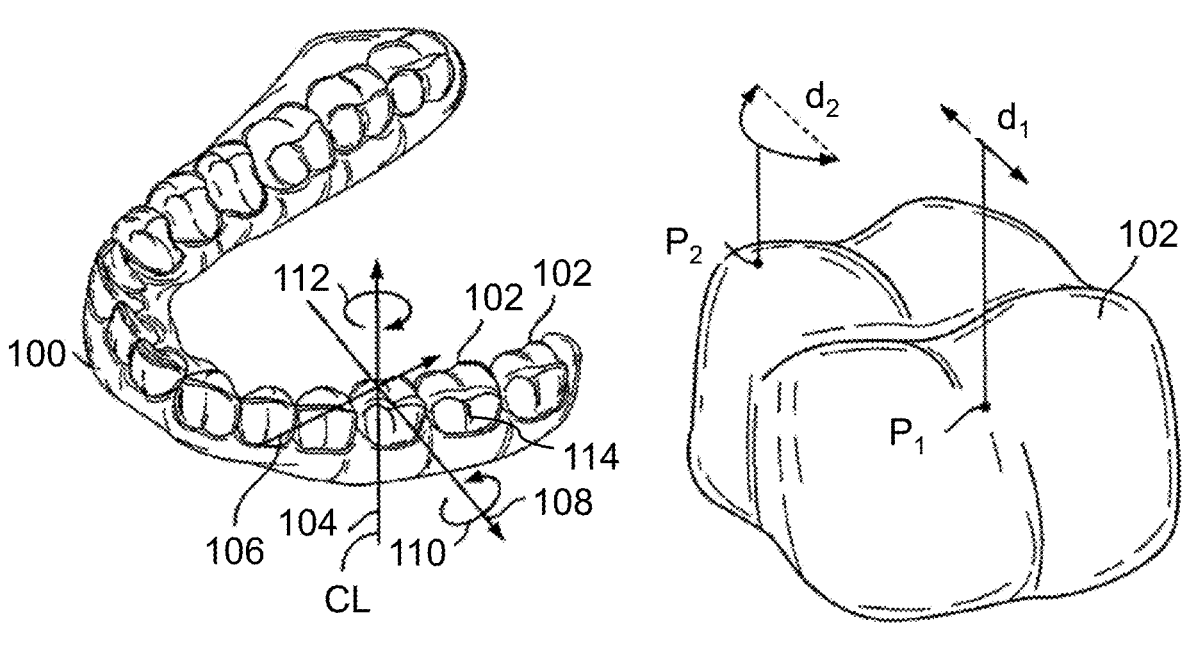
FIG. 2A                    FIG. 2B

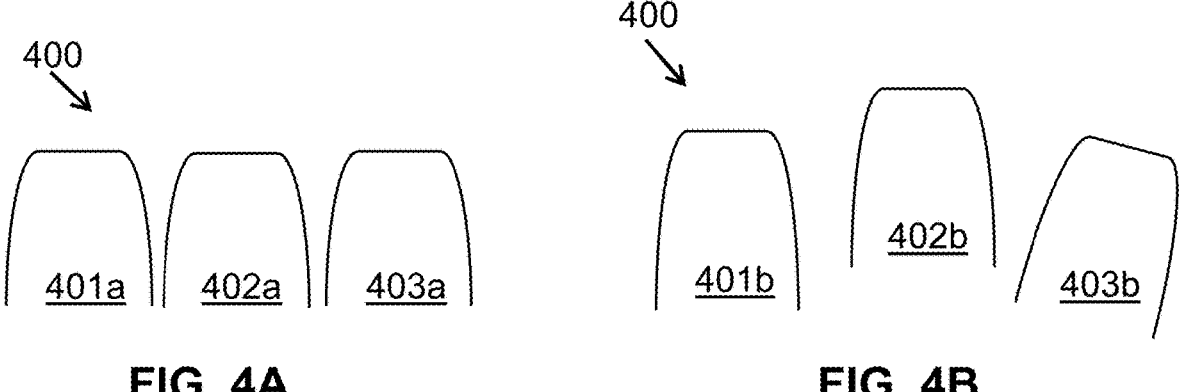
FIG. 4A
FIG. 4B
400
401b 401a          412  412      402b 403a  413
411          411              413
FIG. 4C
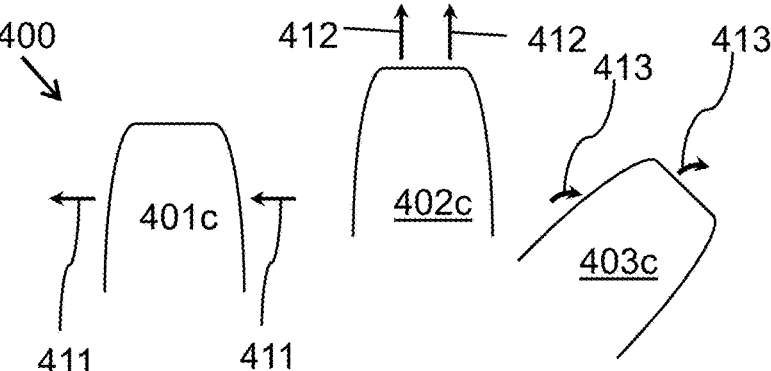
FIG. 4D

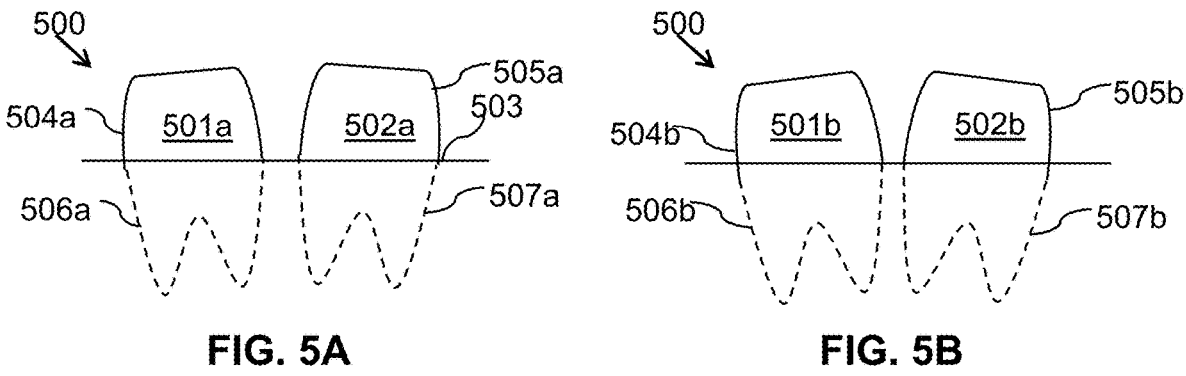
FIG. 5A                              FIG. 5B
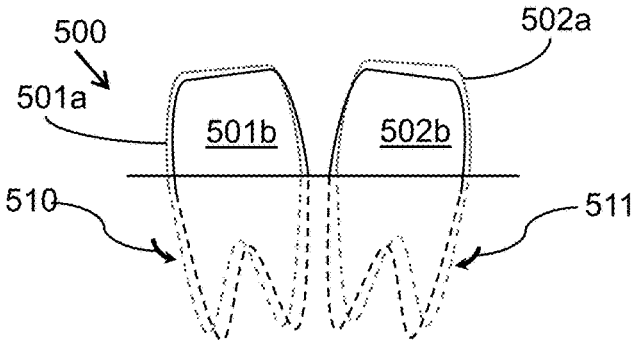
FIG. 5C
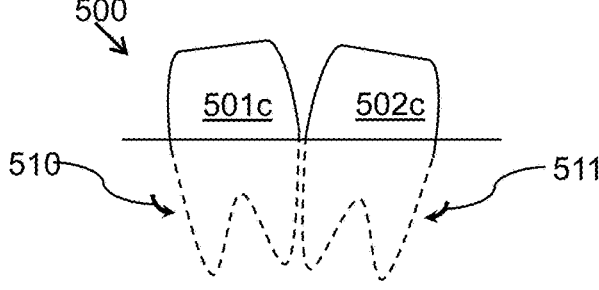
FIG. 5D

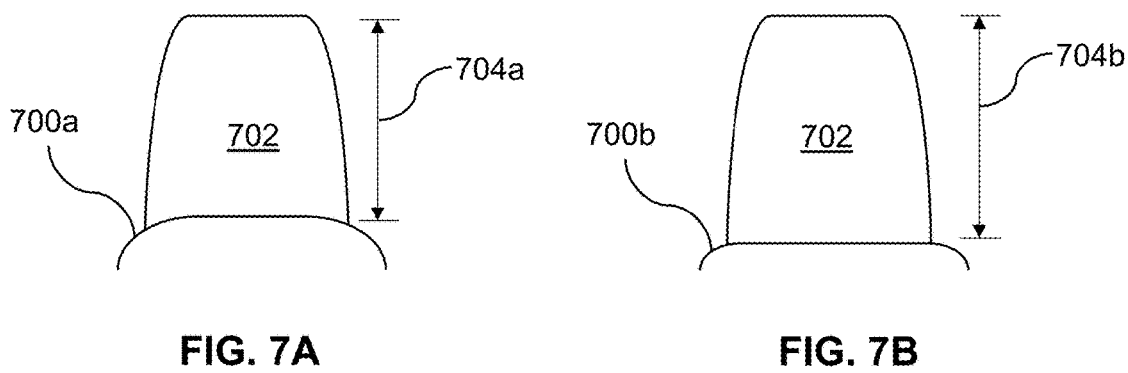
FIG. 7A                                FIG. 7B
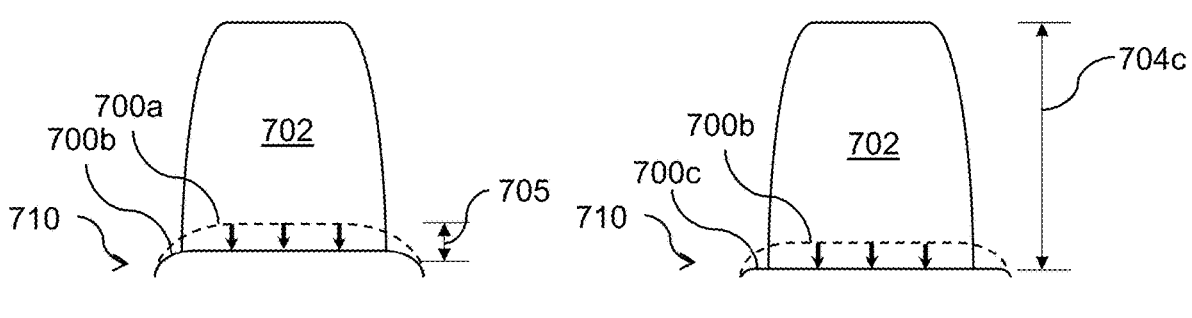
FIG. 7C                                FIG. 7D

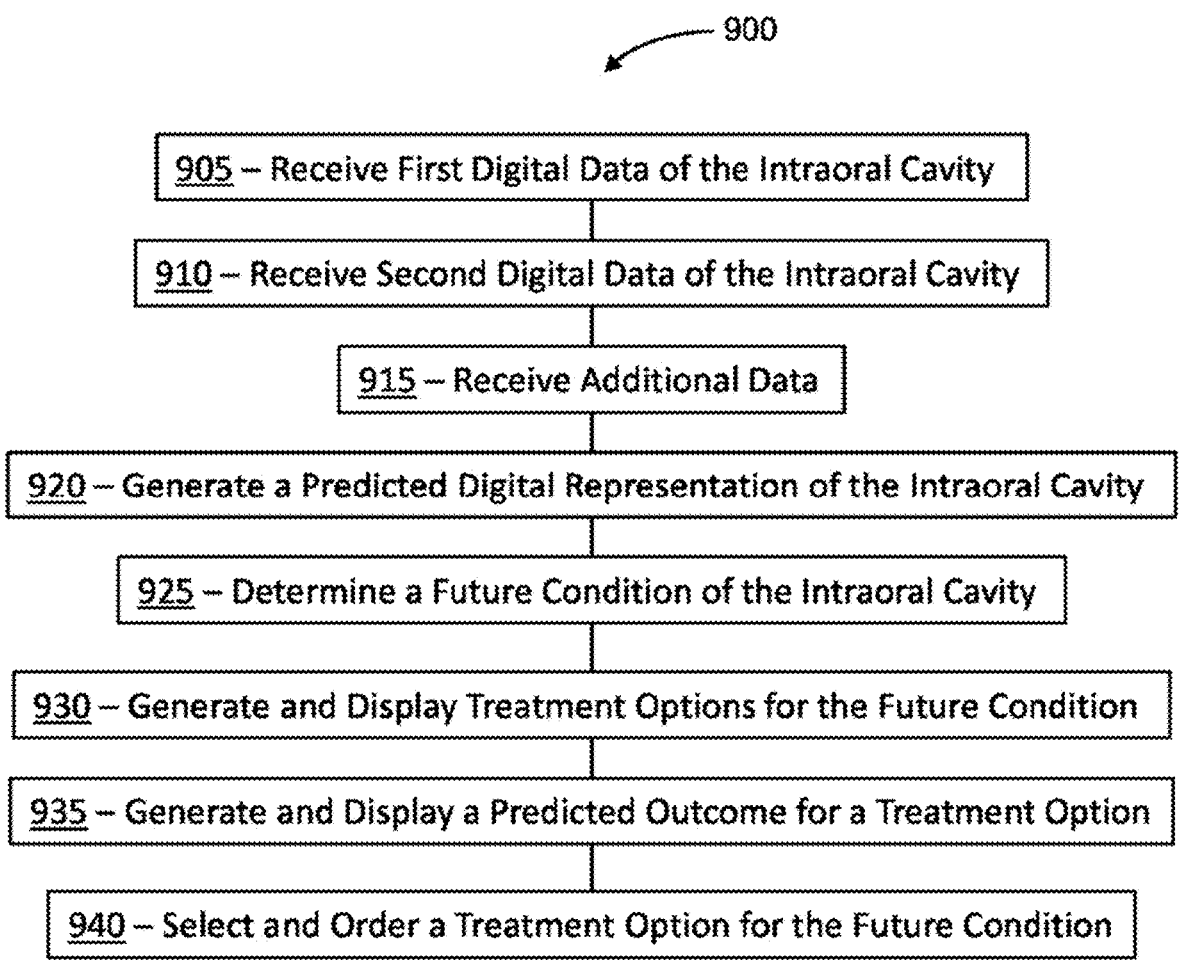

905 – Receive First Digital Data of the Intraoral Cavity

910 – Receive Second Digital Data of the Intraoral Cavity

915 – Receive Additional Data

920 – Generate a Predicted Digital Representation of the Intraoral Cavity

925 – Determine a Future Condition of the Intraoral Cavity

930 – Generate and Display Treatment Options for the Future Condition

935 – Generate and Display a Predicted Outcome for a Treatment Option

940 – Select and Order a Treatment Option for the Future Condition

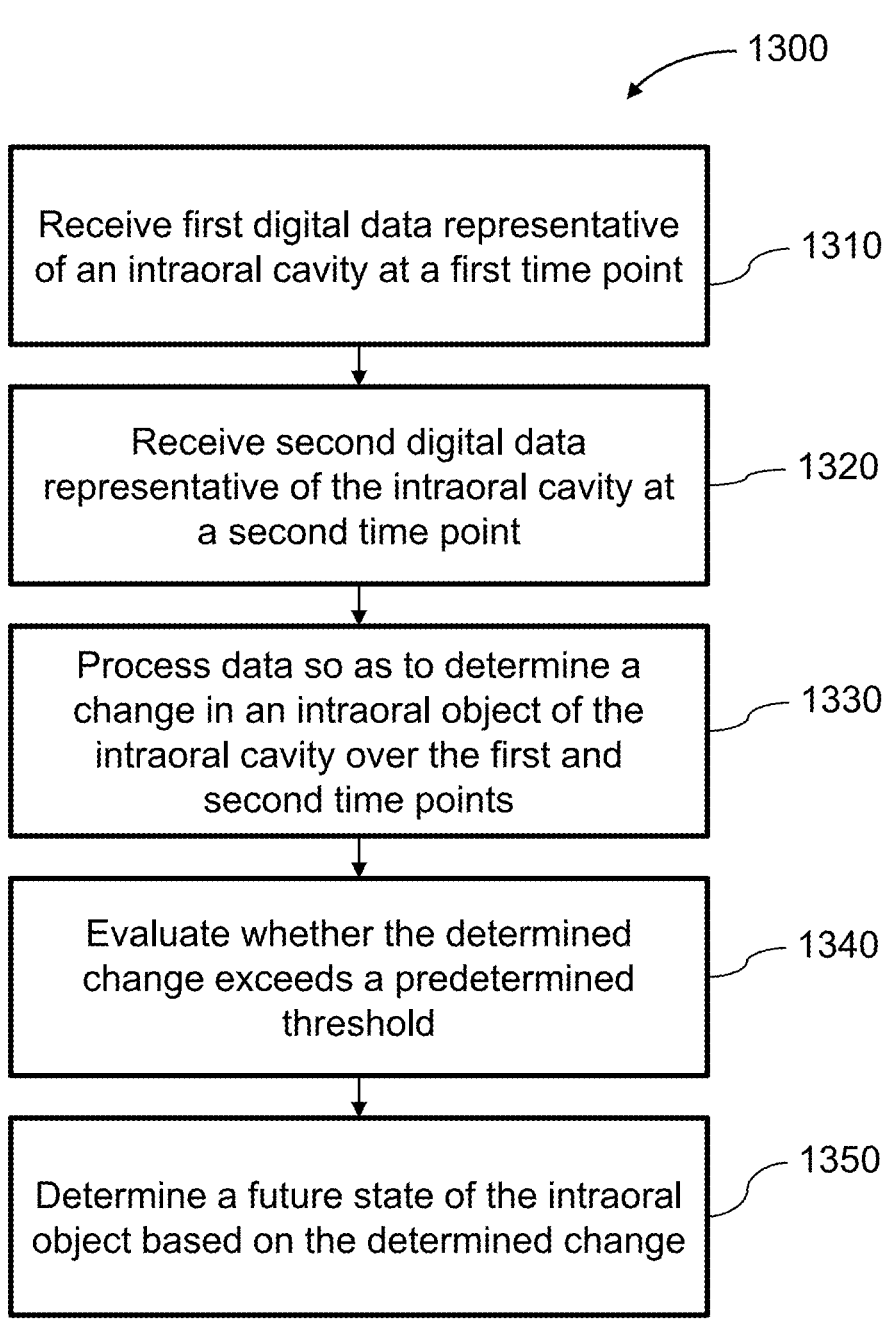

1300

Receive first digital data representative of an intraoral cavity at a first time point — 1310

Receive second digital data representative of the intraoral cavity at a second time point — 1320

Process data so as to determine a change in an intraoral object of the intraoral cavity over the first and second time points — 1330

Evaluate whether the determined change exceeds a predetermined threshold — 1340

Determine a future state of the intraoral object based on the determined change — 1350

FIG. 13

METHOD FOR TRACKING, PREDICTING, AND PROACTIVELY CORRECTING MALOCCLUSION AND RELATED ISSUES

CROSS-REFERENCE

This application is a continuation of U.S. application Ser. No. 14/804,153, filed Jul. 20, 2015, which claims the benefit of U.S. Provisional Application No. 62/079,451, filed Nov. 13, 2014, which both applications are incorporated herein by reference in their entirety.

BACKGROUND

Prior methods and apparatus for identifying and characterizing orthodontic conditions can be less than ideal in at least some instances. For example, prior practices may reactively diagnose and treat orthodontic conditions only after the patient is already experiencing symptoms (e.g., pain, malocclusion), and may be less than ideal for proactively identifying and correcting future conditions that have yet to occur. Additionally, while a medical professional can identify orthodontic conditions by visual examination in some instances, the quantity and rate of change to a patient's dentition may not be as easily characterized and communicated. To name a few examples, the medical professional may indicate that the patient's teeth may continue to be more crooked, that positioning between teeth may continue to increase, that wear on the enamel on the teeth may continue to worsen (e.g., in the case of bruxism), that the patient's jaw may lock up, that the patient may have difficulty sleeping (e.g., in the case of sleep apnea), or that gum surgery may be necessary (e.g., where the recession of gingiva is identified). The medical professional, however, may have difficulty in determining the specific, subtle changes that will occur, as well future conditions that may arise as a result of these changes. Moreover, prior methods can be less than ideal for monitoring and predicting changes in the patient's dentition that are not detectable by visual examination (e.g., changes to the roots of the teeth).

Prior technology to characterize and report the subtle changes associated with many orthodontic conditions can be less than ideal in at least some instances. For example, prior technologies may not allow the medical professional or patient to visualize (e.g., in three dimensions) any projected progression of the orthodontic condition. Other technologies may only present a static view of the orthodontic conditions and provide no predictive information.

In light of the above, it would be desirable to provide improved methods and apparatus for tracking, predicting, and proactively correcting dental or orthodontic conditions such as malocclusion. Ideally, such methods and apparatus would allow changes to a patient's dentition to be accurately identified, predicted, quantified, and visualized.

SUMMARY

Embodiments of the present disclosure provide systems, methods, and devices for predicting future dental or orthodontic conditions in a patient. In some embodiments, digital data representative of the patient's intraoral cavity at a plurality of different time points is received and used to generate a predicted digital representation of the intraoral cavity at a future time point. For example, the digital data can be used to determine and extrapolate changes to one or more intraoral objects (e.g., teeth, gums, airway) to the future time point, thus providing predictions with improved accuracy compared to predictions based on visual examination only. A future undesirable dental or orthodontic condition in the patient can be determined based on the predicted digital representation, thus allowing for the condition to be preemptively diagnosed and treated before the condition has actually occurred or has progressed to a more advanced state. Additionally, the systems, methods, and devices herein can be used to generate one or more treatment options for a predicted condition in order to facilitate decision making by the patient and/or practitioner. Optionally, a digital representation of the predicted results obtained with a selected treatment option can be generated and displayed in order to provide further guidance to the patient and/or practitioner. Advantageously, the approaches provided herein enable proactive diagnosis and correction of various dental or orthodontic conditions, which may be advantageous for reducing treatment cost, duration, and/or difficulty.

In one aspect, a computer-implemented method for calculating a future position of an intraoral object of a patient's intraoral cavity comprises receiving first digital data representative of an actual state of the intraoral cavity at a first time point and receiving second digital data representative of an actual state of the intraoral cavity at a second time point different from the first time point. The method can comprise processing data including the first and second digital data so as to determine a velocity of an intraoral object of the intraoral cavity over the first and second time points. A future position of the intraoral object at a future time point can be determined based on the velocity. The future position can be determined prior to the intraoral object being in the future position.

Other objects and features of the present disclosure will become apparent by a review of the specification, claims, and appended figures.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 1 is an elevational diagram showing the anatomical relationship of the jaws of a patient, according to various embodiments;

FIG. 2A shows in more detail the patient's lower jaw and provides a general indication of how teeth may move, according to various embodiments;

FIG. 2B shows a single tooth from FIG. 2A and defines how tooth movement distances can be determined, according to various embodiments;

FIG. 4A shows a schematic of a set of teeth, according to various embodiments;

FIG. 4B shows a schematic of the set of teeth of FIG. 4A which have moved, according to various embodiments;

FIG. 4C shows a schematic of the set of teeth of FIG. 4A compared to the set of teeth of FIG. 4B to determine the position change to the set of teeth, according to various embodiments;

FIG. 4D shows a schematic of projected future positions of the set of teeth of FIG. 4B based on the trajectories and magnitudes of changes previously determined, according to various embodiments;

FIG. 5A shows a schematic of a set of teeth including the roots, according to various embodiments;

FIG. 5B shows a schematic of the set of teeth of FIG. 5A which have moved, according to various embodiments;

FIG. 5C shows a schematic of the set of teeth of FIG. 5A compared to the set of teeth of FIG. 5B to determine the position change to the set of teeth based on the root movement, according to various embodiments;

FIG. 5D shows a schematic of projected future positions of the set of teeth of FIG. 5B based on the trajectories and magnitudes of changes previously determined, according to various embodiments;

FIG. 7A shows a schematic of a gingival line, according to various embodiments;

FIG. 7B shows a schematic of the gingival line of FIG. 7A which has its position and shape changed over time, according to various embodiments;

FIG. 7C shows a schematic of the gingival line of FIG. 7A compared to that of FIG. 7B to determine the position and shape change of the gingival line, according to various embodiments;

FIG. 7D shows a schematic of a projected future position and shape of the gingival line of FIG. 7B based on the shape change trajectories and magnitudes previously determined, according to various embodiments;

FIG. 9 shows a method for generating a predicted digital representation of a patient's intraoral cavity in order to determine a future condition in the patient, according to various embodiments;

FIG. 11A illustrates a user interface predicting conditions including minor spacing and minor rotation over time, and solutions including a refinement retainer; FIG. 11B illustrates a user interface predicting conditions including minor spacing, minor rotation, major rotation, gingiva recession, and minor crowding, with accompanying solutions including mild orthodontia, rinse and floss, and surgery; FIG. 11C illustrates a user interface predicting conditions over a selected number of years with accompanying solutions; FIG. 11D illustrates a user interface predicting various conditions with accompanying solutions with assigned values; FIG. 11E illustrates a user interface displaying a comparison of digital data of the patient's intraoral cavity; FIG. 11F illustrates a user interface displaying a model of the patient's arches in occlusion; FIG. 11G illustrates a user interface displaying a digital model of a solution for sleep apnea.

FIG. 13 shows a method for calculating a change in an intraoral object in order to determine a future state of the intraoral object, according to various embodiments.

DETAILED DESCRIPTION

Figure 3:
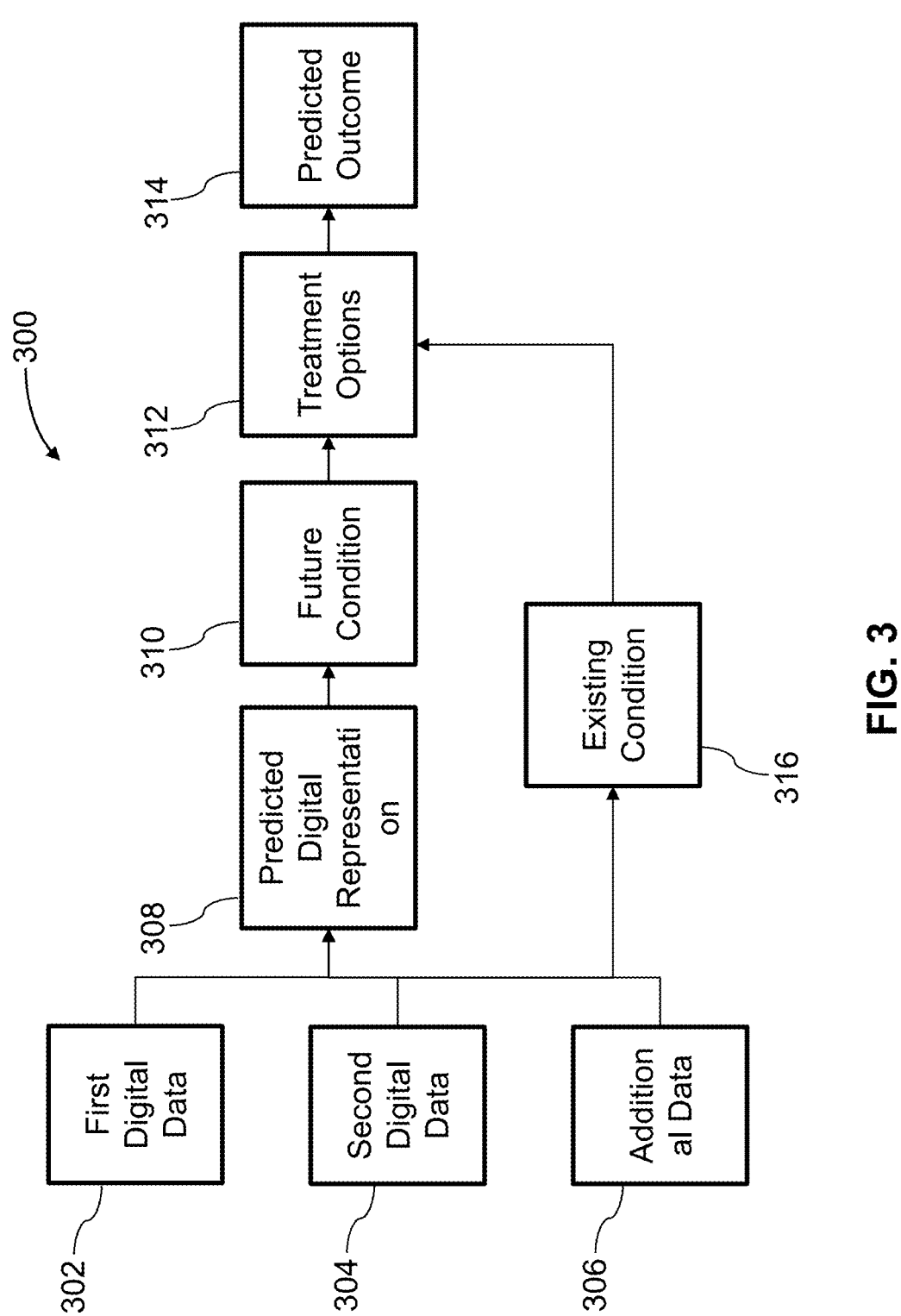
FIG. 3 shows a system for predicting a future dental or orthodontic condition in a patient, according to various embodiments.

The present disclosure provides improved and more effective methods and systems for early detection and/or prediction of a dental or orthodontic condition. The methods and apparatus disclosed herein can be combined in many ways and used to diagnose or treat one or more of many intraoral conditions. In some embodiments, the methods and apparatus herein can be used to detect and predict various types of dental or orthodontic conditions that may arise in a patient, determine suitable treatment products and/or procedures for preventing or correcting the condition, and/or show the predicted results of administering the treatment products and/or procedures. A predictive method can involve comparing surface scan data and/or sub-surface data of the teeth at a plurality of time points in order to determine changes to the position and/or shape of the teeth over time, then generating a prediction of the future position and/or shape of the teeth, based on the determined changes, for example.

Such methods can provide improved predictive accuracy compared to methods which rely upon visual examination or static data only. Changes to the intraoral cavity can be difficult to visually assess based on photos, study casts, and/or notes from previous clinical examinations, because changes may often be subtle and/or progress slowly, among other issues. Even changes based on intraoral scanning may be difficult to detect visually without the assistance of digital geometric assessment, since the differences between the scans may be extremely minute. However, such minute changes over time are cumulative and may develop into larger, more significant issues given enough time. These issues may be prevented, reduced, or resolved based upon use of the embodiments of the present disclosure.

With the methods and systems of the present disclosure, dental or orthodontic condition(s) may be identified and predicted before they become more serious and/or less easily treatable. In children, for example, as primary teeth are lost and permanent teeth are replacing them, potentially crowded teeth can be identified early and the appropriate treatment timed and applied with less force (e.g., because the teeth may not yet be as attached strongly to the bone structures of the mouth or the erupting teeth are smaller or less massive.) In contrast to conventional reactive treatment approaches, the predictive methods of the present disclosure permit detection of dental or orthodontic conditions before the condition has actually occurred or has progressed to a more severe state, thus allowing the medical professional to anticipate and proactively start treatment at an earlier stage. Advantageously, treatments for early stage orthodontic or dental conditions may be less difficult, aggressive, costly, time-consuming, and/or painful than those for conditions detected in later stages.

In one aspect, a computer-implemented method for calculating a future position of an intraoral object of a patient's intraoral cavity comprises receiving first digital data representative of an actual state of the intraoral cavity at a first time point and receiving second digital data representative of an actual state of the intraoral cavity at a second time point different from the first time point. The method can comprise processing data including the first and second digital data so as to determine a velocity of an intraoral object of the intraoral cavity over the first and second time points. A future position of the intraoral object at a future time point can be determined based on the velocity. The future position can be determined prior to the intraoral object being in the future position In some embodiments, the first and second digital data each comprise one or more of surface data or sub-surface data of the intraoral cavity.

In some embodiments, the method further comprises displaying a graphical representation of the intraoral object in the future position of the intraoral object on a user interface shown on a display.

In some embodiments, the method further comprises determining a positional change of the intraoral object between the first and second time points, based on the first and second digital data; and evaluating whether the positional change exceeds a predetermined threshold. The predetermined threshold can be received or determined in various ways. For instance, the predetermined threshold can be input by a user. Alternatively or in combination, the predetermined threshold can be determined based on one or more of user preferences, patient characteristics, or values from dental or orthodontic literature. The predetermined threshold may be indicative of an undesirable dental or orthodontic condition, for example.

If the positional change exceeds the predetermined threshold, various actions can be performed. In some embodiments, the method further comprises outputting an alert to a user in response to an evaluation that the positional change exceeds the predetermined threshold. Alternatively or in combination, the method can further comprise generating a plurality of options for producing a desired dental or orthodontic outcome, in response to an evaluation that the positional change exceeds the predetermined threshold. The plurality of options can be displayed on a user interface shown on a display. The plurality of options can comprise a plurality of treatment options for an undesirable dental or orthodontic condition. In some embodiments, displaying the plurality of options comprises displaying one or more of pricing information, treatment time information, treatment complication information, or insurance reimbursement information associated with each of the plurality of treatment options.

The present disclosure is applicable to various types of intraoral objects located in and/or associated with the intraoral cavity. For example, the intraoral object can comprise one or more of a tooth crown, tooth root, gingiva, airway, palate, tongue, or jaw. The method can further comprise processing data including the first and second digital data so as to determine a rate of change in one or more of a shape, size, or color of the intraoral object. For instance, the intraoral object can comprise a tooth and the rate of change can comprise a tooth shape change velocity. As another example, the intraoral object can comprise gingiva and the rate of change can comprise a gingival shape change velocity.

The systems, methods, and devices presented herein can be used to predict linear and/or non-linear movements of an intraoral object. In some embodiments, determining a future position of the intraoral object comprises determining a movement trajectory of the intraoral object based on the velocity. The movement trajectory may be linear. In some embodiments, the method further comprises determining a movement trajectory of the intraoral object based on the velocity over the first, second, and third time points. The movement trajectory may be non-linear. The non-linear movement trajectory can comprise one or more of a change in movement direction or a change in movement speed, for example. A future position of the intraoral object can be determined based on the non-linear movement trajectory. Optionally, the method further comprises processing data including the first, second, and third digital data so as to determine a force vector associated with the intraoral object over the first, second, and third time points.

In some embodiments, the method further comprises generating a predicted digital representation of the intraoral cavity at a future time point subsequent to the first and second time points, based on the future position of the intraoral object.

In some embodiments, determining the future position of the intraoral object comprises extrapolating the velocity to the future time point using linear or non-linear extrapolation.

In some embodiments, the method further comprises determining a future condition of the intraoral cavity based on the future position of the intraoral object. The future condition can comprise an undesirable dental or orthodontic condition that is predicted to occur at the future time point if the intraoral cavity is left untreated. The future condition can be determined prior to occurrence of the future condition.

In some embodiments, one or more of the receiving the first digital data, receiving the second digital data, processing the data, or determining the future position is performed with aid of one or more processors.

In another aspect, a computer system for calculating a future position of an intraoral object of a patient's intraoral cavity comprises one or more processors and memory. The memory can comprise instructions that, when executed by the one or more processors, cause the system to receive first digital data representative of an actual state of the intraoral cavity at a first time point and receive second digital data representative of an actual state of the intraoral cavity at a second time point different from the first time point. The instructions can cause the system to process data including the first and second digital data so as to determine a velocity of an intraoral object of the intraoral cavity over the first and second time points. The instructions can cause the system to determine a future position of the intraoral object at a future time point based on the velocity, wherein the future position is determined prior to the intraoral object being in the future position.

In another aspect, a computer-implemented method for calculating a positional change over time of an intraoral object of a patient's intraoral cavity comprises receiving first digital data representative of an actual state of the intraoral cavity at a first time point and receiving second digital data representative of an actual state of the intraoral cavity at a second time point different from the first time point. The method can comprise processing data including the first and second digital data so as to determine a positional change of the intraoral object between the first and second time points. The method can comprise evaluating whether the positional change exceeds a predetermined threshold.

In some embodiments, the method further comprises outputting an alert to a user in response to an evaluation that the positional change exceeds the predetermined threshold. Optionally, the method can comprise generating a plurality of options for producing a desired dental or orthodontic outcome, in response to an evaluation that the positional change exceeds the predetermined threshold and displaying the plurality of options on a user interface shown on a display. The predetermined threshold can be determined based on one or more of user preferences, patient characteristics, or values from dental or orthodontic literature.

In another aspect, a computer system for calculating a positional change over time of an intraoral object of a patient's intraoral cavity comprises one or more processors and memory. The memory can comprise instructions that, when executed by the one or more processors, cause the system to receive first digital data representative of an actual state of the intraoral cavity at a first time point and receive second digital data representative of an actual state of the intraoral cavity at a second time point different from the first time point. The instructions can cause the system to process data including the first and second digital data so as to determine a positional change of the intraoral object between the first and second time points. The instructions can cause the system to evaluate whether the positional change exceeds a predetermined threshold.

In another aspect, a method for generating a predicted digital representation of a patient's intraoral cavity in order to determine a future condition in the patient is provided. The method can comprise receiving first digital data representative of the intraoral cavity at a first time point and receiving second digital data representative of the intraoral cavity at a second time point different from the first time point. A predicted digital representation of the intraoral cavity at a future time point subsequent to the first and second time points can be generated based on the first and second digital data. A future condition of the intraoral cavity can be determined in response to the predicted digital representation. The future condition can comprise an undesirable dental or orthodontic condition that is predicted to occur at the future time point if the intraoral cavity is left untreated. The future condition can be determined prior to occurrence of the future condition.

Various types of digital data are suitable for use with the present disclosure. In some embodiments, the first and second digital data each comprise three-dimensional data of the intraoral cavity. Alternatively or in combination, the first and second digital data can each comprise two-dimensional data of the intraoral cavity. In some embodiments, the first and second digital data each comprise one or more scans of the intraoral cavity. The first and second digital data can each comprise surface data of the intraoral cavity, and the surface data can comprise scan data representative of a three-dimensional surface topography of the intraoral cavity.

Alternatively or in combination, the first and second digital data can each comprise sub-surface data of the intraoral cavity. The sub-surface data can comprise one or more of X-ray data, cone beam computed tomography (CBCT) data, CAT scan data, magnetic resonance imaging (MM) data, or ultrasound data. For instance, the sub-surface data can comprise a representation of one or more roots of the patient's teeth. Accordingly, the predicted digital representation of the intraoral cavity can comprise a predicted digital representation of the one or more roots at the future time point based on the sub-surface data, and the future condition can be determined based on the predicted digital representation of the one or more roots. Optionally, the sub-surface data comprises a representation of one or more of an airway, a jaw, or a bone of the patient.

In some embodiments, the first and second time points are different by at least 1 month, at least 3 months, at least 6 months, or at least 1 year. The future time point can be at least 1 month, at least 3 months, at least 6 months, at least 1 year, at least 2 years, or at least 5 years subsequent to the first and second time points.

Digital data from a plurality of different time points can be obtained and analyzed in order to monitor the progression of the patient's intraoral cavity over time and predict its future state. For instance, in some embodiments, the method further comprises receiving third digital data representative of the intraoral cavity at a third time point different from the first and second time points. The predicted digital representation can be generated based on the first, second, and third digital data.

The predictive approaches herein can utilize other types of data in addition to digital data of the intraoral cavity. In some embodiments, the method further comprises receiving additional data of the patient, and the predicted digital representation is generated based on the additional data. The additional data can comprise one or more of demographic information, lifestyle information, medical information, medical history, familial medical history, or genetic factors.

The predictive techniques discussed herein can be implemented in many ways. In some embodiments, generating the predicted digital representation comprises generating a comparison of the first and second digital data. Generating the comparison can comprise registering the first and second digital data to each other in a common coordinate system. Optionally, generating the comparison comprises measuring a characteristic of an intraoral object at the first time point, measuring the characteristic of the intraoral object at the second time point, and determining a change to the characteristic of the intraoral object between the first and second time points. The intraoral object can comprise one or more of a tooth or a gum, and the characteristic can comprise one or more of a position, an orientation, a shape, a size, or a color of the tooth or gum, for example.

In some embodiments, the method further comprises comparing the measured characteristic at one or more of the first or second time points to measured characteristics from a patient information database. The comparing of the measured characteristic at one or more of the first or second time points to the measured characteristics from the patient information database can be based on one or more of demographic information, lifestyle information, medical information, medical history, familial medical history, or genetic factors.

Changes to one or more intraoral objects can be used as a basis for predicting a future state of the patient's intraoral cavity. For instance, in some embodiments, the method further comprises predicting a future change to the characteristic of the intraoral object in response to the determined change, and the predicted digital representation is generated based on the future change. The future change can be predicted in response to a selected interval of time.

In some embodiments, the predicted digital representation is generated in response to the determined change to the characteristic of the intraoral object between the first and second time points. Determining the change to the characteristic can comprise determining one or more of a tooth movement velocity, a tooth shape change velocity, a tooth size change velocity, or a gingival shape change velocity. For instance, generating the predicted digital representation can comprise determining a rate of change of the characteristic of the intraoral object, based on the determined change between the first and second time points. The rate of change can be extrapolated to the future time point so as to predict the characteristic of the intraoral object at the future time point.

The present disclosure can be used to predict a future state of various types of intraoral objects, such as the future positions of one or more teeth. In some embodiments, for example, the predicted digital representation represents the patient's teeth in a predicted arrangement at the future point. Accordingly, generating the predicted digital representation can comprise generating a first digital model representing the patient's teeth in a first arrangement at the first time point, generating a second digital model representing the patient's teeth in a second arrangement at the second time point, and calculating tooth movement velocities for one or more teeth between the first and second arrangements. The one or more teeth of the second digital model can be repositioned according to the tooth movement velocities in order to generate the predicted arrangement of the patient's teeth at the future time point. Optionally, repositioning the one or more teeth of the second digital model can comprise detecting a collision that occurs between the one or more teeth during repositioning of the one or more teeth and modifying the tooth movement velocities in response to the detected collision.

Many different types of dental or orthodontic conditions can be predicted using the embodiments provided herein. In some embodiments, the undesirable dental or orthodontic condition comprises one or more of: malocclusion, tooth decay, loss of one or more teeth, root resorption, periodontal disease, gingival recession, a temporomandibular joint disorder, bruxism, a blocked airway, or sleep apnea. The future condition can be determined by measuring one or more parameters of the predicted digital representation that are indicative of the undesirable dental or orthodontic condition. The one or more parameters can comprise one or more of: an amount of overbite, an amount of underbite, an amount of tooth tipping, an amount of tooth extrusion, an amount of tooth intrusion, an amount of tooth rotation, an amount of tooth translation, an amount of tooth spacing, an amount of tooth crowding, an amount of tooth wear, an amount of gum recession, a jaw width, or a palate width. In some embodiments, the method further comprises comparing the one or more parameters to one or more threshold values in order to determine whether the undesirable dental or orthodontic condition is predicted to occur at the future time point. An alert can be generated if an abnormality is detected in the one or more parameters. Optionally, the method can further comprise generating a user interface shown on a display, the user interface being configured to display the one or more parameters.

The results of the predictive techniques presented herein can be displayed to a user. In some embodiments, the method further comprises generating a user interface shown on a display. The user interface can be configured to display a predicted three-dimensional model representative of the predicted digital representation of the intraoral cavity at the future time point. The user interface can be configured to display a first three-dimensional model representative of the intraoral cavity at the first time point and a second three-dimensional model representative of the intraoral cavity at the second time point. Optionally, the user interface is configured to display an overlay of two or more of the first three-dimensional model, the second three-dimensional model, or the predicted three-dimensional model.

Once a future condition has been identified, potential treatment options can be generated and displayed to the user. Accordingly, in some embodiments, the method further comprises generating one or more treatment options for the future condition and displaying the one or more treatment options on the user interface shown on the display. The one or more treatment options can comprise a list of one or more treatment products or procedures for the future condition. The list of one or more treatment products or procedures can comprise one or more of pricing information, treatment time information, treatment complication information, or insurance reimbursement information. Optionally, the method can further comprise generating a comparison of the one or more treatment options and displaying the comparison on the user interface shown on the display. Generating the comparison can comprise comparing one or more of treatment efficacy, cost, duration, or predicted outcome.

Some embodiments of the present disclosure provide predictions of treatment outcomes that may be achieved by administering one or more treatment options to the patient. In some embodiments, the method further comprises generating a second predicted digital representation of the intraoral cavity following administration of at least one of the one or more treatment options, and displaying a second predicted three-dimensional model representative of the second predicted digital representation using the user interface shown on the display over time.

In some embodiments, the method further comprises receiving user input selecting at least one treatment option of the one or more treatment options via the user interface shown on the display and generating an order for the at least one treatment option in response to the received user input. Optionally, the order is generated based on one or more of the first or second digital data.

In another aspect, a system for generating a predicted digital representation of a patient's intraoral cavity in order to determine a future condition in the patient is provided. The system can comprise one or more processors and memory. The memory can comprise instructions executable by the one or more processors in order to cause the system to receive first digital data representative of the intraoral cavity at a first time point and receive second digital data representative of the intraoral cavity at a second time point different from the first time point. The instructions can cause the system to generate a predicted digital representation of the intraoral cavity at a future time point subsequent to the first and second time points based on the first and second digital data. The instructions can cause the system to determine a future condition of the intraoral cavity in response to the predicted digital representation. The future condition can comprise an undesirable dental or orthodontic condition that is predicted to occur at the future time point if the intraoral cavity is left untreated. The future condition can be determined prior to occurrence of the future condition.

In some embodiments, the system further comprises a display, and the instructions cause the display to generate a user interface. The user interface can be configured to display one or more of: a predicted three-dimensional model representative of the predicted digital representation of the intraoral cavity, a first three-dimensional model representative of the intraoral cavity at the first time point, a second three-dimensional model representative of the intraoral cavity at the second time point, or one or more treatment options for the future condition. In some embodiments, the user interface is configured to display the one or more treatment options and receive user input selecting at least one treatment option of the one or more treatment options. Optionally, the user interface is configured to display a second predicted three-dimensional model representative of a second predicted digital representation of the intraoral cavity following administration of the at least treatment option. In some embodiments, the user interface is configured to display a comparison of the one or more treatment options.

Although certain embodiments herein are presented in the context of predicting future tooth arrangements, this is not intended to be limiting, and it shall be appreciated that the systems, methods, and devices of the present disclosure can also be applied to extrapolate the future state of other types of intraoral tissues or objects, such as the gingiva, jaws, palate, tongue, and/or airway.

Turning now to the drawings, FIG. 1 shows a skull 10 with an upper jawbone 22 and a lower jawbone 20. The lower jawbone 20 hinges at a joint 30 to the skull 10. The joint 30 is called a temporomandibular joint (TMJ). The upper jawbone 22 is associated with an upper jaw 101, while the lower jawbone 20 is associated with a lower jaw 100.

A computer model of the jaws 100 and 101 can be generated, and a computer simulation models interactions among the teeth on the jaws 100 and 101. The computer simulation can allow the system to focus on motions involving contacts between teeth mounted on the jaws. The computer simulation can allow the system to render realistic jaw movements which are physically correct when the jaws 100 and 101 contact each other. Further, the model can be used to simulate jaw movements including protrusive motions, lateral motions, and "tooth guided" motions where the path of the lower jaw 100 is guided by teeth contacts rather than by anatomical limits of the jaws 100 and 101. Motions can be determined for one jaw, but may also be determined for both jaws to represent the bite.

Referring now to FIG. 2A, the lower jaw 100 includes a plurality of teeth 102, for example. At least some of these teeth may be moved from an initial tooth arrangement to a subsequent tooth arrangement. As a frame of reference describing how a tooth has been moved, an arbitrary centerline (CL) may be drawn through the tooth 102. With reference to this centerline (CL), each tooth movement may be tracked in orthogonal directions represented by axes 104, 106, and 108 (where 104 is the centerline). The centerline may be rotated about the axis 108 (root angulation) and the axis 104 (torque) as indicated by arrows 110 and 112, respectively. Additionally, the tooth may be rotated about the centerline. Thus, all possible free-form motions of the tooth can be tracked. These motions include translation (e.g., movement in one or more of the X-axis or Y-axis), rotation (e.g., movement about the Z-axis), extrusion (e.g., movement in the Z-axis), or tipping (e.g., movement about one or more of the X-axis or Y-axis), to name a few. In addition to teeth movement, the movement of the gum line 114 may also be tracked using models such as model 100. In some embodiments, the model includes X-ray information of the jaw so that movements of the roots of the teeth can be tracked as well.

FIG. 2B shows how the magnitude of any tooth movement may be defined in terms of a maximum linear translation of any point P on a tooth 102. Each point P1 may undergo a cumulative translation as that tooth is moved in any of the orthogonal or rotational directions defined in FIG. 2A. That is, while the point will usually follow a nonlinear path, there can be a linear distance between any point in the tooth when determined at any two times during the treatment. Thus, an arbitrary point P1 may in fact undergo a true side-to-side translation as indicated by arrow d1, while a second arbitration point P2 may travel along an arcuate path, resulting in a final translation d2. Many aspects of the present disclosure may be defined in terms of the maximum permissible movement of a point P1 induced on any particular tooth. Such maximum tooth movement, in turn, can be defined as the maximum linear translation of that point P1 on the tooth which undergoes the maximum movement for that tooth in any treatment step.

The present disclosure provides systems, methods, and devices for monitoring and tracking changes to the one or more structures of the intraoral cavity, including but not limited to the teeth, gingiva, jaws, TMJ joint, tongue, palate, and airway. Examples of such changes include one or more of: movement of one or more teeth (e.g., extrusion, intrusion, rotation, torqueing, tipping, or translating); changes to the size, shape, and/or color of one or more teeth; changes to the size, shape, and/or color of the gingiva associated with one or more teeth; changes to the occlusal relationship ("bite") between the upper and lower jaws; changes to the width of the jaws and/or palate; changes to the positioning of the tongue; or changes to the shape of the airway.

In some embodiments, the changes in the patient's intraoral cavity can result in and/or be indicative of one or more dental or orthodontic conditions. As used herein, the term "condition" refers to a disease, disorder, or other undesirable, abnormal, and/or dysfunctional state manifesting in a patient. Examples of such conditions include but are not limited to: malocclusion (e.g., tooth crowding, tooth spacing, an overbite, an overjet, an underbite, a crossbite, an open bite), tooth decay, loss of one or more teeth, root resorption, periodontal disease (e.g., gingivitis, periodontitis), gingival recession, a temporomandibular joint disorder, bruxism, a blocked airway, and sleep apnea. A condition as used herein can be differentiated from unsatisfactory or unsuccessful results of a treatment or other therapeutic intervention (e.g., deviation of teeth from a prescribed tooth arrangement in an orthodontic treatment plan, failure of a sleep apnea treatment to achieve the intended results, etc.).

In some embodiments, certain changes in the intraoral cavity are indicative of and/or associated with a future undesirable dental or orthodontic condition that has yet to occur. For instance, certain tooth movements, if allowed to progress, may result in a future malocclusion. As another example, certain changes in the shape of the gingiva may be indicative of future gum recession. In yet another example, insufficient width of the patient's dental arches and/or palate may be associated with an increased likelihood of sleep apnea, e.g., due to posterior displacement of the tongue. In yet another example, changes to the coloration of the teeth and/or gingiva may be indicative of tooth decay and/or periodontal disease.

Accordingly, the present disclosure provides systems, methods, and devices for predicting a future condition in a patient by monitoring and tracking changes to the intraoral cavity over time. In some embodiments, data of the intraoral cavity is captured over multiple different time points in order to detect changes in the intraoral cavity. Based on the detected changes, a prediction of the state of the intraoral cavity (e.g., positioning, shape, size, etc. of one or more objects in the intraoral cavity) at a future time point can be made. The predicted future state can be analyzed to identify any future dental or orthodontic conditions that may occur at the future time point, such as a future malocclusion, tooth decay, loss of one or more teeth, root resorption, periodontal disease, gingival recession, a temporomandibular joint disorder, bruxism, a blocked airway, and/or sleep apnea. Once a future condition has been identified, potential treatment options (e.g., for preventing or correcting the condition) can be generated and presented to the practitioner and/or patient for review. In some embodiments, these approaches are implemented using computer-based methods with digital modeling in order to enable detection of changes to the intraoral cavity and prediction of future conditions with increased sensitivity and accuracy compared to conventional visual examination.

In some embodiments, the systems, methods, and devices of the present disclosure are used to predict a future condition prior to the occurrence of the future condition. For instance, some embodiments herein may be used to predict a future malocclusion of the patient's teeth, even though the patient's current tooth arrangement is normal. As another example, some embodiments herein may be used to predict that a patient will suffer from sleep apnea in the future, even though the patient is not currently experiencing any sleep apnea events. The approaches herein allow for prediction of future dental or orthodontic conditions months or even years before the condition would actually manifest in the patient, thus enabling such conditions to be preemptively and pro-actively treated.

FIG. 3 illustrates a system 300 for predicting a future dental or orthodontic condition in a patient. The system 300 includes a plurality of data sets representative of the patient's intraoral cavity at a plurality of different time points, such as first digital data 302 representative of the intraoral cavity at a first time point and second digital data 304 representative of the intraoral cavity at a second time point (e.g., subsequent to the first time point). If desired, digital data for additional time points (e.g., third digital data for a third time point, fourth digital data for a fourth time point, etc.) can also be included. The digital data can provide a representation of an actual state of one or more intraoral objects (e.g., teeth, gingiva, jaws, TMJ joint, tongue, palate, etc.), such as a representation of the positioning, shape, size, coloration, etc. of the intraoral object at the particular time point. For example, the first digital data 302 can include a three-dimensional model representing the arrangement of one or more teeth and/or gingiva at the first time point, and the second digital data 304 can include a three-dimensional model representing the arrangement of the one or more teeth and/or gingiva at the second time point. Alternatively or in combination, the digital data can provide data for other portions of the intraoral cavity besides the teeth and sur-rounding tissues, such as the patient's jaws or airway. Such data can provide a more complete understanding of how the various structures of the intraoral cavity may interact to produce a dental or orthodontic condition, as well as how these interactions may be corrected to reduce or treat a dental or orthodontic condition. For instance, treatment of sleep apnea may involve corrections to the positions of teeth (e.g., palate expansion to move the tongue forward) as well as corrections to the patient's jaws and bite alignment (e.g., mandibular advancement to tighten the tissues of the air-way). It shall be appreciated that data representing an actual state of the intraoral cavity can be differentiated from data representing projected, desired, or ideal states of the intraoral cavity, e.g., data representing a state that is desired to be achieved by administration of a dental or orthodontic therapy, such as a targeted arrangement of teeth in an orthodontic treatment plan.

Various types of digital data are suitable for use with the embodiments presented herein, such as two-dimensional data (e.g., photographs, radiographs, or other types of images) or three-dimensional data (e.g., scan data, surface topography data, three-dimensional models constructed from two-dimensional data). The digital data can be static (e.g., images) or dynamic (e.g., video). The digital data can provide a representation of the size, shape, and/or surface topography of one or more intraoral objects, such as scans or images depicting the positions and orientations of the patient's teeth, gingiva, etc. Additionally, the digital data can also provide a representation of the spatial relationships (e.g., relative positions and orientations) of different intraoral objects to each other, such as bite registration data indicative of the occlusal relationship between the upper and lower jaws, cephalometric analysis data, facebow measure-ment data indicative of the position of the TMJ relative to the dental arches, etc. Multiple different types of digital data can be combined with each other in order to form a digital model that accurately represents the patient's intraoral surface and/or subsurface cavity at a specified time point. For example, two-dimensional data can be combined with three-dimensional data, as discussed further herein.

In some embodiments, the digital data includes scan data of the patient's intraoral cavity, such as one or more three-dimensional scans. Three-dimensional intraoral scans may be taken, for example, using an intraoral scanner that utilizes confocal focusing of an array of light beams to determine surface topography (e.g., the iTero™ and iOC™ scanning systems available from Align Technology, Inc. of San Jose, CA). The scan data can provide a digital representation of the three-dimensional surface topography of intraoral objects such as the teeth and/or gingiva. With three-dimen-sional intraoral scans, for example, small changes in the dentition can be accurately captured and visualized in a relatively non-invasive manner. Three-dimensional intraoral scans may use no ionizing radiation, making the procedure very safe relative to other techniques which may use X-rays (e.g., cone beam computed tomography (CBCT) or CAT scans). Three-dimensional intraoral scans may also have the accuracy and resolution (e.g., 20-50 microns) sufficient to detect minor or minute changes that may be difficult to detect with alternative methods (e.g., dentition impressions such as with silicone or alginate, visual examination). In some embodiments, the scan data is segmented in order to separate individual teeth from each other and/or from the gingiva so as to provide manipulable three-dimensional representations of each tooth. Alternatively, unsegmented scan data can be used.

In some embodiments, the digital data provides surface data that represents one or more visible external surfaces of the intraoral cavity (e.g., tooth surfaces located above the gingival line such as tooth crowns, gingival surfaces, tongue, etc.). Surface data can be obtained using intraoral scanning as discussed above and herein. Alternatively or in combination, the digital data can provide sub-surface data representing one or more sub-surface structures of the intraoral cavity (e.g., portions of teeth located below the gingival line such as tooth roots, bones, muscles, jaws, airway, etc.) that are not visible in surface scan data. Sub-surface data can include one or more of X-ray data (e.g., bitewings, periapical X-rays, cephalographs, panographs), CBCT data, CAT scan data, magnetic resonance imaging (MM) data, or ultrasound data. Sub-surface data can be two-dimensional (e.g., images) or three-dimensional (e.g., volumetric data).

In some embodiments, sub-surface data can be combined with surface data in order to generate a three-dimensional digital representation of the intraoral cavity including both surface and sub-surface structures. For example, the surface data and the sub-surface data can be combined to generate a three-dimensional representation of the entire tooth structure including crowns, roots, and gingiva. Data of the roots of the teeth may be helpful for improving understanding of tooth movements, particularly with respect to non-linear changes in the movement velocity and/or direction, and therefore can be beneficial in predicting future tooth movements with greater accuracy. For example, collisions of tooth roots, root shape changes due to decay or resorption, etc., can influence the movements of the teeth. Some type of tooth movements may be "root-first" movements in which the root leads the corresponding movement of the crown. In some embodiments, three-dimensional surface data of one or more tooth crowns can be obtained using scanning. Three-dimensional sub-surface data of one or more tooth roots corresponding to the tooth crowns can be obtained using CBCT scan data. Alternatively or in combination, two-dimensional X-ray images or other images can be stitched together to form a three-dimensional representation of the tooth roots. Optionally, the tooth crown data and tooth root data can each be segmented into separate tooth components in order to allow the components to be manipulated individually. The tooth crown data and tooth root data can then be digitally combined to generate a three-dimensional model of the entire teeth, e.g., using surface matching. In some embodiments, a surface matching algorithm uses surface data of the tooth crowns to match and orient the tooth root data to the correct position for each tooth. Matching can be performed in three-dimensional space based on landmarks (e.g., gingival edges, occlusal surface ridges). The accuracy and speed of the matching can vary based on the amount of surface data used in the matching procedures. Once the roots are matched and in the correct position, the algorithm can sample the data of the roots to create root surface data. The root surface data can then be stitched to the crown surface data to generate the tooth model.

The time points at which the digital data is generated and/or obtained can be varied as desired. For instance, each time point may be different by at least 1 month, at least 2 months, at least 3 months, at least 4 months, at least 5 months, at least 6 months, at least 7 months, at least 8 months, at least 9 months, at least 10 months, at least 11 months, at least 1 year, at least 2 years, at least 5 years, or any other extended time interval sufficient for accurate detection of changes and/or predictions. The intervals between each time point may be the same or may vary, as desired. Optionally, the intervals between time points can be shorter for patients in which more changes are expected to occur (e.g., pediatric patients) and longer for patients in which fewer changes are expected to occur (e.g., adult patients). In some embodiments, each digital data set is obtained at a different time point, while in other embodiments, at least some of the digital data sets can be obtained at the same time point. In some embodiments, the digital data is obtained during regular dental checkups (e.g., annual or semi-annual checkups) such that the time points correspond to the timing of the checkups. Optionally, the digital data can be obtained before and/or after a surgical procedure on the patient's intraoral cavity, in which case it may be beneficial to obtain digital data at very short time intervals for more accurate monitoring.

Optionally, the system 300 can include one or more sets of additional data 306. The additional data 306 can include any data of the patient that is potentially relevant to dental or orthodontic health, such as demographic information (e.g., age, sex, race), lifestyle information (e.g., physical activity levels, smoking status, drug intake status, alcohol intake status, dietary habits, oral hygiene habits), medical information (e.g., height, weight, body mass index (BMI)), medical history, familial medical history, and/or genetic factors. These patient-specific factors may influence the likelihood that certain dental or orthodontic conditions will occur, for example. The additional data can be obtained at a single time point or at a plurality of different time points, and the time point(s) may or may not correspond to the time points for the digital data 302, 304.

In some embodiments, the digital data and/or additional data used for generating predictions as discussed herein include one or more of the following items: two-dimensional images, three-dimensional images, three-dimensional images generated from one or more two-dimensional images, CBCT data, three-dimensional scan data, video data, cephalometric analysis data, plaster model analysis data, growth predictions, bite relations, historical data of similar patients and/or treatments, race, gender, age, dietary habits, whether the patient experiences difficulty sleeping, whether the patient snores, sleep apnea diagnosis data, titration test data for oral sleep appliances, bruxism, and/or analysis data from the treating professional.

The first digital data 302, second digital data 304, and/or additional data 306 are used to generate a predicted digital representation 308 of the patient's intraoral cavity. The predicted digital representation 308 can be a two-dimensional or three-dimensional model of the patient's intraoral cavity at a future time point subsequent to the first and second time points. The future time point can be at least 1 month, at least 2 months, at least 3 months, at least 4 months, at least 5 months, at least 6 months, at least 7 months, at least 8 months, at least 9 months, at least 10 months, at least 11 months, at least 1 year, at least 2 years, at least 5 years, at least 10 years, at least 20 years, or any other desired length of time subsequent to the last time point at which digital data was obtained. In some embodiments, the predicted digital representation 308 indicates a predicted state (e.g., positioning, shape, size, coloration, etc.) of one or more intraoral objects at the future time point.

The predicted digital representation 308 can be generated in a variety of ways. In some embodiments, a comparison of digital data of the intraoral cavity at a plurality of different time points (e.g., first digital data 302 and second digital data 304) is generated in order to determine changes to the intraoral cavity over time. For instance, one or more characteristics (e.g., position, orientation, shape, size, color) of one or more intraoral objects (e.g., teeth, gingiva, jaws, TMJ, palate, airway) can be measured at each of a plurality of different time points using the digital data. By comparing measurements obtained at different time points, the rates, magnitudes, directions, locations, etc. of changes to the intraoral objects can be determined. These changes can then be extrapolated to the future time point in order to predict the future state of the intraoral object. Accordingly, the predicted digital representation 308 of the intraoral cavity can be generated by repeating this process for each intraoral object of interest. Exemplary methods for generating the predicted digital representation 308 are described in greater detail below.

Alternatively or in combination, the predicted digital representation 308 can be generated based on a comparison of the patient data (e.g., the digital data, additional data, measured characteristics, determined changes) to historical data of similar patients (e.g., stored in a patient information database). The historical data can be data of patients with characteristics that are similar to or closely match the situation of the current patient, for example. The similarities may include bite, teeth positions, teeth shapes, teeth movement velocities, teeth shape change velocities, to name a few. Optionally, similarity may be based on the additional patient-specific factors described herein, e.g., patients with similar demographic information, lifestyle information, medical information, medical history, familial medical history, and/or genetic factors. The determined changes to the intraoral cavity of the patient may be compared to data regarding similar changes of similar patients available from a patient database. In some embodiments, the determined rates, magnitudes, directions, and or locations of the changes to the one or more intraoral objects may be adjusted based on the historical patient data. The historical patient data can be used to predict the future outcome of the changes in the patient's intraoral cavity in order to generate the predicted digital representation 308.

The predicted digital representation 308 is used to predict a future condition 310 of the patient's intraoral cavity. As discussed above and herein, the future condition 310 can be an undesirable dental or orthodontic condition (e.g., malocclusion, tooth decay, loss of one or more teeth, root resorption, periodontal disease, gingival recession, a TMJ disorder, bruxism, a blocked airway, sleep apnea, etc.) that is predicted to occur at the future time point if the intraoral cavity is left untreated. "Untreated" as used herein refers to absence of treatment for the particular condition and does not necessarily imply that the patient is not receiving treatment for other conditions. For example, the future condition 310 can be a malocclusion that is predicted to occur in the future if the patient does not receive treatment to correct or prevent the malocclusion. As another example, the future condition 310 can be gingival recession that is predicted to occur in the future if the patient does not receive treatment to correct or prevent the gingival recession.

In some embodiments, the future condition 310 is predicted by analyzing the predicted digital representation 308 to identify whether any undesirable dental or orthodontic conditions are present at the future time point. For example, the positions of one or more teeth in the predicted digital representation 308 can be evaluated to determine whether there is a malocclusion. As another example, the location of a gingival line in the predicted digital representation 308 can be assessed to determine whether an excessive amount of gum recession has occurred. Optionally, one or more parameters indicative of an undesirable condition can be measured using the predicted digital representation 308, such as an amount of overbite, an amount of underbite, an amount of tooth tipping, an amount of tooth extrusion, an amount of tooth intrusion, an amount of tooth rotation, an amount of tooth translation, an amount of tooth spacing, an amount of tooth crowding, an amount of tooth wear, an amount of gum recession, a jaw width, and/or a palate width. The measured parameters can be compared to expected ranges and/or threshold values for the parameters in order to determine whether an undesirable condition will occur at the future time point.

Based on the predicted future condition 310, one or more treatment options 312 can be generated. The treatment options can include products and/or procedures for correcting and/or preventing the predicted dental or orthodontic condition. Exemplary treatment products include but are not limited to corrective appliances (e.g., tooth repositioning appliances such as aligners or braces, retainers, sleep apnea devices, mouth guards, dental splints, bite plates), implants and restorations (e.g., prosthetics such as crowns or bridges, fillings), and medications (e.g., antibiotics, mouthwash, toothpaste). Exemplary treatment procedures include but are not limited to corrective surgery (e.g., orthognathic surgery, periodontal surgery), modification of the dentition and/or other intraoral objects (e.g., orthodontia, tooth extraction, space maintenance, space supervision, space regaining, interproximal reduction (IPR), distillation, palate expansion, occlusal adjustments), modification of oral hygiene habits (e.g., brushing, flossing, use of mouthwash), and lifestyle modifications (e.g., dietary habits, physical activity level, smoking status, drug intake status, alcohol intake status).

Some examples of dental or orthodontic conditions and the corresponding treatment options include the following: a blocked airway or sleep apnea (e.g., a sleep apnea device such as a mandibular advancement appliance, corrective surgery, palate expansion, etc.), teeth crowding (e.g., tooth extraction, IPR, distillation, palate expansion, tooth extraction, orthodontia, etc.), at least one missing tooth (e.g., closure, implants, corrective surgery, etc.), a tooth spacing issue (e.g., closure, IPR, extraction, palate expansion, corrective surgery, etc.), gum disease (e.g., corrective surgery, recommendation of better hygiene, mouth wash, etc.), gum recession (e.g., corrective surgery, recommendation of better hygiene, mouth wash, etc.), a TMJ disorder (e.g., jaw repositioning surgery, jaw repositioning apparatus, etc.), a bite misalignment (e.g., corrective surgery, corrective appliance, etc.), an overbite (e.g., corrective appliance, orthodontia, etc.), a crossbite (e.g., corrective appliance, arch expansion, orthodontia, etc.), an open bite (e.g., corrective appliance, corrective surgery, orthodontia, etc.), an overjet (e.g., corrective appliance, orthodontia, etc.), an underbite (e.g., corrective appliance corrective surgery, orthodontia, etc.), a malocclusion (e.g., space maintenance, space supervision, or space regaining, corrective surgery, orthodontia, etc.), root resorption (e.g., implants, etc.), or bruxism (e.g., corrective appliance, occlusal adjustment, etc.).

The treatment options 312 can be provided as a list of treatment products and/or procedures. Optionally, the list can also include one or more of pricing information, treatment time information, treatment complication information, or insurance reimbursement information for the treatment options. The treatment options listed may be ranked in many ways such as by effectiveness as a therapy, costs, treatment time, appropriateness for the patient or patient, or insurance reimbursement, to name a few. The list may also include hyperlinks to preferred vendors and/or medical professionals for the therapeutic products and/or procedures. For example, airway issues may be identified, and one or more airway specialists may be recommended.

Optionally, a predicted outcome 314 of one or more treatment options can be generated. The predicted outcome 314 can represent a predicted state (e.g., positioning, shape, size, coloration, etc.) of one or more intraoral objects at the future time point subsequent to administration of a selected treatment option. The future time point can be at least 1 month, at least 2 months, at least 3 months, at least 4 months, at least 5 months, at least 6 months, at least 7 months, at least 8 months, at least 9 months, at least 10 months, at least 11 months, at least 1 year, at least 2 years, at least 5 years, at least 10 years, at least 20 years, or any other desired length of time subsequent to the administration of the treatment option. The future time point can be determined based on a patient activity or life event (e.g., wedding, vacation, business trip, etc.). In some embodiments, generating the predicted outcome 314 involves generating one or more models (e.g., two-dimensional or three-dimensional models) representing the patient's intraoral cavity after treatment is applied.

The predicted treatment outcome 314 can be generated using various techniques. For instance, the outcome 314 can be generated based on previously obtained data of the patient's intraoral cavity and/or other relevant patient data, e.g., the first digital data 302, second digital data 304, and/or additional data 306. In some embodiments, the treatment outcome 314 is determined based on a comparison to historical data of similar patients, e.g., patients with characteristics that are similar to the current patient, for example. Optionally, historical treatment data representing outcomes of similar treatments can be used to predict the outcome of applying the treatment to the current patient.

Optionally, in some embodiments, an existing condition 316 of the patient's intraoral cavity is also determined. The existing condition can be an undesirable dental or orthodontic condition (e.g., malocclusion, tooth decay, loss of one or more teeth, root resorption, periodontal disease, gingival recession, a temporomandibular joint disorder, bruxism, a blocked airway, sleep apnea, etc.) that has already occurred and is currently present in the patient's intraoral cavity. In some embodiments, the existing condition 316 is predicted by analyzing previous and/or current data of the patient's intraoral cavity (e.g., the first digital data 302 and second digital data 304) to identify whether any undesirable dental or orthodontic conditions are currently present. The identification of existing conditions from digital data can be performed similarly to the identification of a future condition from a predicted digital representation discussed above and herein. Treatment options 312 and/or predicted outcomes 314 for the existing condition 316 can also be generated, similar to the procedures discussed herein for the future condition 310. It shall be appreciated that embodiments herein presented in the context of detecting and treating a predicted future condition are equally applicable to the detection and treatment of an existing condition.

As discussed above and herein, a predicted digital representation of a patient's intraoral cavity at a future time point can be generated by comparing digital data of the intraoral cavity obtained at different time points. In some embodiments, the digital data is compared in order to determine changes to one or more characteristics (e.g., positioning, size, shape, color, etc.) of an intraoral object over time. Various methods can be used to compare digital data sets to each other in order to identify changes to intraoral objects. In some embodiments, two or more sets of digital data are registered to each other within a common coordinate system. The approaches herein can be used to register a two-dimensional digital data set to another two-dimensional digital data set (e.g., two images), a three-dimensional digital data set to another three-dimensional digital set (e.g., two three-dimensional models), and/or a two-dimensional digital data set to a three-dimensional digital data set or vice-versa (e.g., an image to a three-dimensional model), as desired. By registering the data to each other in a single coordinate system, a reference frame for measurement is established.

For instance, digital data of teeth obtained at different time points (e.g., the stitched three-dimensional models of tooth crowns and tooth roots discussed herein) can be processed to determine unique identifiers or identifying landmarks, such as the tips or edges of teeth, or the Facial Axis of the Clinical Crown (FACC). These identifiers can be matched to corresponding identifiers in the other digital representations in order to determine the transformation that has occurred between the different time points. Alternatively or in combination, surface matching algorithms can be used to register the digital data to each other. In some embodiments, a matching process positions two teeth approximately based on each crown center and tooth local coordinate system. Then, for each tooth, a matching operation is performed. The matching operation can be an iteration process that minimizes an error value while trying to find the appropriate tooth location. In some embodiments, the process finds a point on the original tooth crown and a corresponding point on the current tooth and calculates the distance between these points. The process then determines a transformation that minimizes the square sum of these errors. The teeth are positioned, and the process is repeated. A new set of points are selected, and the process finds the difference and determines the transformation that minimizes the error. The above steps can be iterated until the error is less than termination criteria or a maximum number of iterations is reached.

Once the digital data are registered to each other, the changes between the different data sets can be determined. For example, initial and subsequent digital data can be superimposed into a common coordinate system to determine in three dimensions the volumetric discrepancies between the data and therefore the changes to the teeth which have taken place between the data. By comparing the magnitude of the change and the time interval over which the change occurs, a rate of change can be determined. In some embodiments, a rate of change can include one or more of a tooth movement velocity, a tooth shape change velocity, a tooth size change velocity, a gingival shape change velocity, and so on. For example, the velocities of tooth shape changes may be calculated where dental wear is identified, and the velocities of gingival shape changes may be calculated where there is identified gingival recession or inflammation. The changes may be represented as one or more vectors indicating a magnitude and/or direction of the change over time.

The predicted digital representation can subsequently be generated by extrapolating the determined rate of change to a future time point. The extrapolation may assume that the intraoral object will continue to change at a rate consistent with the determined rate of change. For instance, in the context of tooth movement, it may be assumed that a tooth will continue moving along the direction and according to the speed specified by the current tooth movement vector unless an obstacle is encountered. Accordingly, extrapolation can be used to predict the trajectory of the tooth and thereby determine its future position. The extrapolation method used may be linear (e.g., the rate of change is assumed to be constant) or non-linear (e.g., the rate of change may vary over time), as discussed further herein. Linear extrapolation can be performed using data from at least two different time points, while non-linear extrapolation can be performed using data from at least three different time points. Non-linear extrapolation can be used to predict tooth movement along a curved path and/or an accelerating or decelerating tooth movement, for example. In some embodiments, non-linear tooth movement may occur if there are collisions of tooth surfaces and/or subsurfaces, or may occur due to changes in the patient's physiology, diet, age, etc.

As an example, FIGS. 4A through 4D show how movement of a set of teeth 400 can be tracked and predicted. The set of teeth 400 may comprise a first tooth, a second tooth, and a third tooth. FIG. 4A shows the first tooth 401a, the second tooth 402a, and the third tooth 403a at an initial time point. FIG. 4B shows the first tooth 401b, the second tooth 402b, and the third tooth 403b at a subsequent time point. As shown in FIG. 4B, the set of teeth 400 have moved from their positions at the initial time point.

As shown in FIG. 4C, the positions of the set of teeth 400 at the initial and subsequent time points can be compared. For example, three-dimensional models of the teeth 400 can be superimposed onto one another and compared. Movement vectors of the teeth between the initial and subsequent time points can be determined. The movement may be a translation of the first tooth between the initial time point (tooth 401a) and subsequent time point (tooth 401b), and a corresponding movement vector 411 may be determined. The movement may be an extrusion of the second tooth between the initial time point (tooth 402a) and subsequent time point (tooth 402b), and a corresponding movement vector 412 may be determined. The movement may be a tipping of the second tooth between the initial time point (tooth 403a) and subsequent time point (tooth 403b), and a corresponding movement vector 413 may be determined.

As shown in FIG. 4D, the movement vectors 411, 412, and 413 may be used to determine the positions of the teeth 400 at a later time point. In some embodiments, an assumption is made that the teeth 400 will continue to move along the trajectories indicated by the movement vectors 411, 412, and 413. For instance, the first tooth 401c may be translated more at the rate indicated by the first movement vector 411, the second tooth 402c may be extruded more at the rate indicated by the second movement vector 412, and the third tooth 403c may be tipped more at the rate indicated by the third movement vector 413. To be clear, the first tooth 401a, the first tooth 401b, and the first tooth 401c are the same first tooth of the set 400 but at different time points, the second tooth 402a, the second tooth 402b, and the second tooth 402c are the same second tooth of the set 400 but at different time points, and the third tooth 403a, the third tooth 403b, and the third tooth 403c are the same third tooth of the set 400 but at different time points.

While translation, extrusion, and tipping are shown in isolation in FIGS. 4A-4D, the teeth may move in other ways such as rotation or in any combination of ways. For example, a tooth may tip and translate, a tooth may extrude and rotate, a tooth may tip, translate, and extrude, to name a few of the possible tooth movements that may be tracked to determine future movement. Tooth movements that may be tracked include one or more of tooth extrusion, intrusion, rotation, torqueing, tipping, or translating. Alternatively or in combination, other types of changes to a tooth can also be tracked using the methods herein, such as root absorption, enamel decay, and/or caries formation.

In some embodiments, movement of a set of teeth can be tracked and predicted using sub-surface data in addition to surface scan data, as discussed above and herein. FIGS. 5A through 5D show how movement of a set of teeth 500 can be tracked and predicted. The set of teeth 500 may comprise a first tooth and a second tooth. FIG. 5A shows the first tooth 501a and the second tooth 502a an initial time point. Each tooth includes a portion above the gingival line 503 (crown 504a and crown 505a, respectively) and a portion below the gingival line 503 (root 506a and root 507a, respectively). FIG. 5B shows the first tooth 501b and the second tooth 502b at a subsequent time point. As shown in FIG. 5B, the set of teeth 500 have moved from their positions at the initial time point, such that the positioning of the crowns 504b, 505b and roots 506b, 507b at the subsequent time point are different from the initial time point. In some embodiments, the positions of the crowns of the teeth 500 at the different time points can be determined using three-dimensional scans, while the positions of the roots of the teeth 500 at the different time points can be determined using other types of data such as sub-surface data (e.g., X-rays, CBCT scans, CT scans, MRI, ultrasound, etc.). Accordingly, the entirety of each tooth including both visible and non-visible portions can be digitally represented, e.g., as three-dimensional models.

As shown in FIG. 5C, the positions of the set of teeth 500 at the initial and subsequent time points can be compared. For example, three-dimensional models of the teeth 500 including both tooth crowns and tooth roots can be superimposed onto one another and compared. The comparison can involve comparing the positions of the crowns of the teeth 500 at the initial and subsequent time points, as well as the positions of the roots of the teeth 500 at the initial and subsequent time points. Movement vectors 510, 511 of the teeth between the initial and subsequent time points can be determined. The movement vectors 510, 511 can be based on the changes in positions of the crowns and/or the roots of the teeth 500. As shown in FIG. 5C, the teeth 500 move over time at the rate and trajectory indicated by the vectors 510, 511. The movement vectors 510, 511 may be used to determine the positions of the teeth 500 at a later time point. For example, as shown in FIG. 5D, if it is assumed that the teeth will continue to move according to the movement vectors 510, 511, a prediction can be made that the first tooth 501c and the second tooth 502c will begin to slow down and collide with each other at a subsequent time point. Optionally, vectors representing the changes in the shape of the roots (e.g., shrinking of roots due to resorption) can also be determined and used to predict a future position of the tooth.

In some embodiments, the future tooth positions are predicted by analyzing and extrapolating the movement and/or shape changes of the roots. This approach can be advantageous compared to methods that rely solely upon surface scan data and thus are limited to the analysis of tooth crowns, as the positioning and structure of the roots can exert a significant influence on the movements of the teeth. Accordingly, combining surface scan data and sub-surface data as described herein to determine changes to the entirety of the tooth structure can improve the accuracy of extrapolating future tooth positions.

Figure 6A:
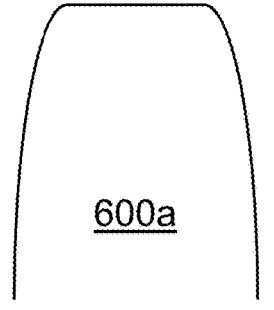
FIG. 6A shows a schematic of a tooth, according to various embodiments.
Figure 6B:
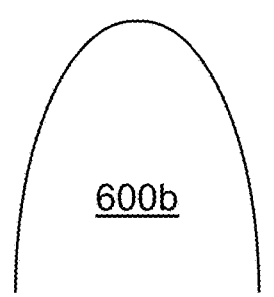
FIG. 6B shows a schematic of the tooth of FIG. 6A which has its shape and size changed over time, according to various embodiments.
Figure 6C:
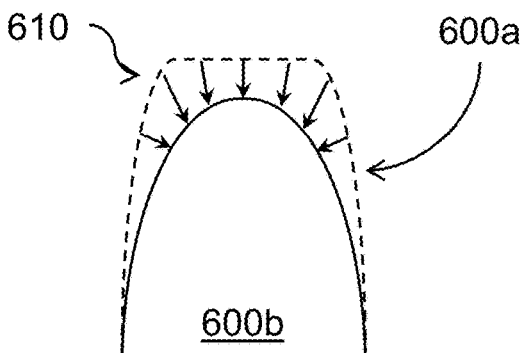
FIG. 6C shows a schematic of the tooth of FIG. 6A compared to that of FIG. 6B to determine the shape and size change to the set of teeth, according to various embodiments.
Figure 6D:
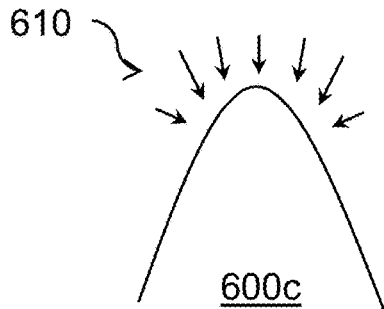
FIG. 6D shows a schematic of a projected future shape of the tooth of FIG. 6B based on the shape and size change trajectories and magnitudes previously determined, according to various embodiments.

As discussed above and herein, shape and/or size changes to teeth may also be determined. Changes to the shape and/or size (e.g., length, width, height, surface area, volume, etc.) of the teeth may be associated with conditions such as bruxism, malocclusion, improper bite alignment, etc. FIG. 6A shows a tooth 600a at an initial point and FIG. 6B shows the same tooth 600b at a subsequent time point. As discussed above and herein, the tooth 600a, 600b can be scanned at the different time points to generate a three-dimensional model of shape and/or size change over time. As shown in FIG. 6C (showing the models of the teeth 600a, 600b superimposed onto one another to show the shape and/or size changes over time), the models of the teeth 600a, 600b can be registered to one another. Vectors 610 for the trajectory and magnitude of the changes can be determined by comparing the surfaces of the teeth 600a and 600b. As shown in FIGS. 6B and 6C, the tooth 600b is worn down over time at the rate and trajectory indicated by the vectors 610. Based on the vectors 610, the future shape and/or size of the tooth 600b, shown as tooth 600c in FIG. 6D, can be determined. For example, it can be assumed that the teeth will continue to be worn down a rate similar to the rate indicated by the vectors 610. Alternatively or in combination, the volumes of the tooth models 600a and 600b can be compared to each other to determine the rate of volume change (e.g., as a percent change relative to the initial volume) of the tooth. The size and/or shape of the future tooth 600*c* can thus be determined by extrapolating the volume change to the future time point.

While a vertical wearing down of the tooth is shown in isolation in FIGS. 6A-6D, other shape and/or size changes such as wearing down of the sides of the tooth as well as combinations thereof can be tracked to determine future movements. Shape and/or size changes may be tracked in combination with tooth movements to determine the shape and position of a tooth at future time points. The predictive approaches described herein can permit earlier and more accurate detection of tooth shape and/or size changes compared to methods that rely on visual examination, thus allowing for earlier diagnosis and correction of conditions such as malocclusion, root absorption, enamel decay, caries formation, etc.

As discussed above and herein, changes to gingiva and other tissues near the teeth may also be determined. Changes to the positioning and/or shape of the gingiva may be associated with gum-related conditions such as gum recession or gingivitis. FIG. 7A shows a gingival line 700*a* of a tooth 702 at an initial point and FIG. 7B shows the same tooth 702 and gingival line 700*b* at a subsequent time point. As discussed above and herein, the tooth 702 and gingival line 700*a*, 700*b* can be scanned at the different time points to generate a three-dimensional model of positional and/or shape change over time. As shown in FIG. 7C (showing the models of the tooth 702 and gingival lines 700*a*, 700*b* superimposed onto one another to show the position and/or shape changes over time), the models of the tooth 702 and gingival line 700*a*, 700*b* can be registered to one another. Vectors 710 for the trajectory and magnitude of the changes in the position and/or shape of the gingival line can be determined. As shown in FIGS. 7B and 7C, the gingival line recedes over time at the rate and trajectory indicated by the vectors 710. Based on the vectors 710, the future position and/or shape of the gingival line 700*b*, shown as gingival line 700*c* in FIG. 7D, can be determined. For instance, the position and/or shape of the future gingival line 700*c* can be calculated based on the assumption that the gingiva will continue to recede according to the vectors 710.

Alternatively or in combination, the trajectory and magnitude of the changes to the gingival line can be determined by tracking the size (e.g., length, width, height, surface area, volume, etc.) of the corresponding tooth 702. For example, an increase in the surface area and/or height (e.g., distance from the crown to the gingival line) of the tooth may indicate gingival recession. As depicted in FIGS. 7A and 7B, the tooth 702 has an initial height 704*a* at the first time point and an increased height 704*b* at the second time point. The difference 705 between heights 704*a*, 704*b* can be used to calculate a height change rate for the tooth 702, as depicted in FIG. 7C. The height change rate can be used to predict a future height 704*c* of the tooth 702 at a future time point, as shown in FIG. 7D. A tooth height exceeding a threshold value may be indicative of gum recession or gingivitis, for example. The predictive approaches described herein can permit earlier and more accurate detection of gingival positioning and/or shape changes compared to other methods (e.g., visual examination, measurement of the gingival gap).

As described above and herein, changes in the shape and/or positioning of an intraoral object (e.g., teeth) can be tracked to determine a current trajectory for the shape change and/or movement of the object. Some of the changes to shape and/or positioning of the intraoral object may be linear and can be tracked by comparing data (e.g., scan data, sub-surface data, etc.) obtained from at least two time points. Some of the changes to shape and/or positioning of the intraoral object may be non-linear (e.g., exponential) and can be tracked by comparing data obtained from at least three time points. Subsequently, linear or non-linear extrapolation techniques can be used to determine a projected trajectory for the object in order to predict the shape and/or positioning at a future time point.

Figure 8A:
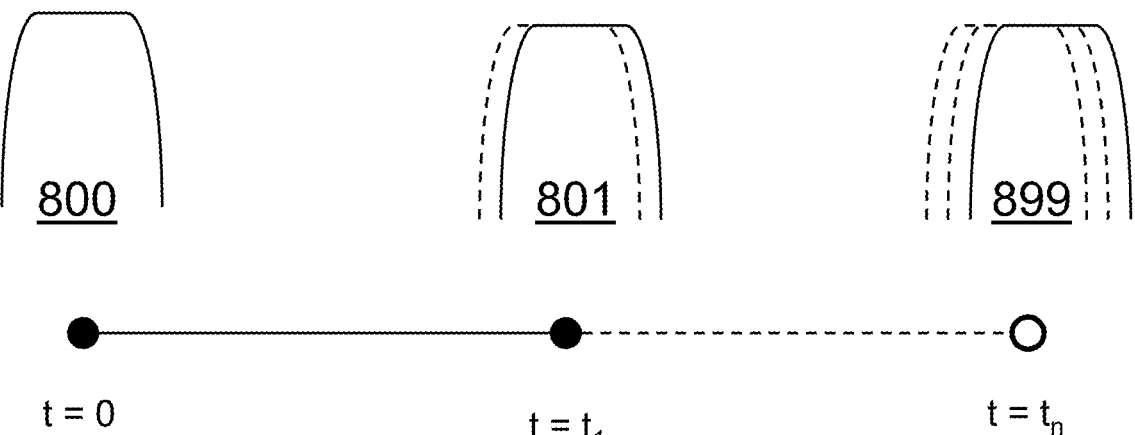
FIG. 8A shows a schematic of a linear extrapolation of a tooth trajectory, according to various embodiments.

FIG. 8A shows a tooth at a first, initial time point 800 (time t=0) and the same tooth at a second, subsequent time point 801 (time t=t₁). As discussed above and herein, scan data (e.g., three-dimensional scans) can be made of the tooth and can be compared to determine how the tooth may change at future points in time. The scan data can be combined with additional data from one or more time points, such as sub-surface data of the roots. The differences between the tooth at the first time point 800 and at the second time point 801 may show that the tooth movement and/or shape change can be defined linearly, and the linear rate of movement and/or shape change may be extrapolated to determine the position and/or shape of the tooth at future time point. FIG. 8A additionally shows the tooth at a future, subsequent time point 899 (time t=t$_n$).

Figure 8B:
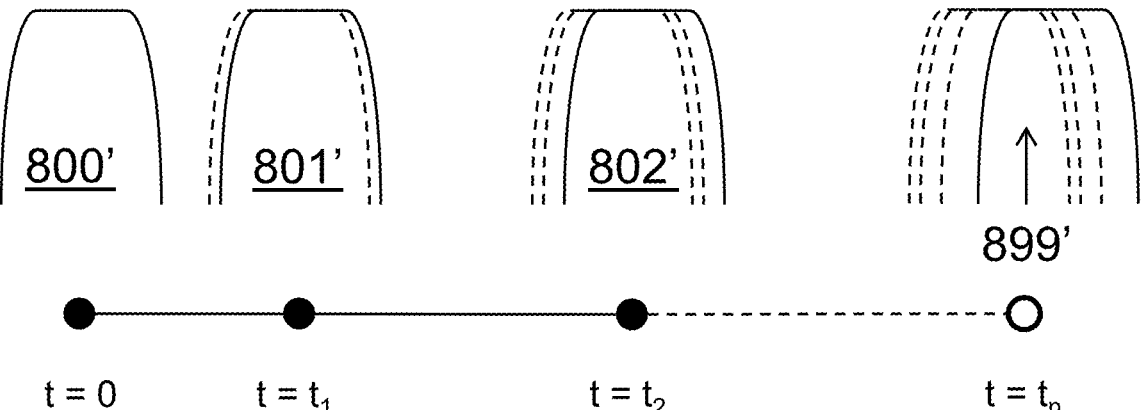
FIG. 8B shows a schematic of a non-linear extrapolation of a tooth trajectory, according to various embodiments.

FIG. 8B shows a tooth at a first, initial time point 800' (time t=0), the same tooth at a second, subsequent time point 801' (time t=t₁), and the same tooth at a third, subsequent time point 802' (time t=t₂). As discussed above and herein, scan data can be made of the tooth and can be compared to determine how the tooth may change at future points in time. The scan data can be combined with additional data from one or more time points, such as sub-surface data of the roots. The differences between the tooth at the first time point 800', at the second time point 801', and at the third time point 802' may show that the tooth movement and/or shape change can be defined non-linearly, and the non-linear rate of movement and/or shape change may be extrapolated to determine the position and/or shape of the tooth at a future time point. FIG. 8B additionally shows the tooth at a future, subsequent time point 899' (time t=t$_n$).

Optionally, the predicted digital representation can be generated using an extrapolation procedure that adjusts the projected trajectory of an intraoral object based on obstacles (e.g., other teeth, colliding roots, bite, root absorption or decay, recession of gums) that the structure may encounter, such as through the use of collision avoidance algorithms as described herein. For example, in some embodiments, digital models of the patient's teeth in different arrangements obtained at different time points are used to generate a predicted digital representation of an arrangement of the patient's teeth at a future time point. Tooth movement velocities for one or more teeth between the different arrangements can be calculated, as discussed herein. Subsequently, the teeth in the digital model can be repositioned according to the calculated velocities in order to generate the future tooth arrangement. During repositioning, a collision detection process can be used to detect whether the projected movements would cause collisions with neighboring teeth. For example, the collision detection process can determine at each time step if any of the geometries describing the tooth surfaces intersect. It may be assumed that the teeth will continue moving according to the calculated movement velocities unless a collision occurs.

Various techniques can be implemented to detect projected collisions between teeth. For example, in some embodiments, a collision detection algorithm is centered around a recursive subdivision of the space occupied by an object, which is organized in a binary-tree like fashion. Triangles are used to represent the teeth in the digital dataset. Each node of the tree is referred to as an oriented bounding box (OBB) and contains a subset of triangles appearing in the node's parent. The children of a parent node contain between them all of the triangle data stored in the parent node.

The bounding box of a node is oriented so it tightly fits around all of the triangles in that node. Leaf nodes in the tree ideally contain a single triangle but can possibly contain more than one triangle. Detecting collisions between two objects involves determining if the OBB trees of the objects intersect. If the OBBs of the root nodes of the trees overlap, the root's children are checked for overlap. The algorithm proceeds in a recursive fashion until the leaf nodes are reached. At this point, a robust triangle intersection routine is used to determine if the triangles at the leaves are involved in a collision.

In some embodiments, OBB trees can be built in a lazy fashion to save memory and time. This approach stems from the observation that some parts of the model will never be involved in a collision, and consequently the OBB tree for such parts of the model need not be computed. The OBB trees are expanded by splitting the internal nodes of the tree as necessary during the recursive collision determination algorithm. Moreover, the triangles in the model which are not required for collision data may also be specifically excluded from consideration when building an OBB tree. For instance, motion may be viewed at two levels. Objects may be conceptualized as "moving" in a global sense, or they may be conceptualized as "moving" relative to other objects. The additional information improves the time taken for the collision detection by avoiding recomputation of collision information between objects which are at rest relative to each other since the state of the collision between such objects does not change.

In alternative embodiments, a collection detection algorithm calculates a "collision buffer" oriented along a z-axis along which two teeth lie. The collision buffer is calculated for each step or at each position along the movement trajectory for which collision detection is desired. To create the buffer, an x, y plane is defined between the teeth. The plane can be "neutral" with respect to the two teeth. Ideally, the neutral plane is positioned so that it does not intersect either tooth. If intersection with one or both teeth is inevitable, the neutral plane is oriented such that the teeth lie, as much as possible, on opposite sides of the plane. In other words, the neutral plane minimizes the amount of each tooth's surface area that lies on the same side of the plane as the other tooth. In the plane is a grid of discrete points, the resolution of which depends upon the required resolution for the collision detection routine. A typical high-resolution collision buffer includes a 400×400 grid; a typical low-resolution buffer includes a 20×20 grid. The z-axis is defined by a line normal to the plane.

The relative positions of the teeth are determined by calculating, for each of the points in the grid, the linear distance parallel to the z-axis between the plane and the nearest surface of each tooth. For example, at any given grid point (M,N), the plane and the nearest surface of the rear tooth are separated by a distance represented by the value $Z1(M,N)$, while the plane and the nearest surface of the front tooth are separated by a distance represented by the value $Z2(M,N)$. If the collision buffer is defined such that the plane lies at z=0 and positive values of z lie toward the back tooth, then the teeth collide when $Z1(M,N)Z2(M,N)$ at any grid point (M,N) on the plane.

If a collision between teeth is detected, the movement velocities and/or trajectories of one or both teeth can be modified. For example, in some embodiments, if a collision occurs, a "push" vector is created to shift the path of the projected movement away from the collision. Based on the push vector, the current tooth "bounces" from the collision and a new tooth movement is generated. Alternatively, it can be assumed that a collision stops some or all further movement of the colliding teeth, e.g., the movement velocities are decreased or set to zero. Optionally, in some embodiments, the extrapolation process is stopped if a collision is detected, e.g., in order to alert the user.

The extrapolation of surface scan data and/or other types of digital data taken at a plurality of different time points can provide earlier and more reliable predictions that are not possible by visual examination or review of static images or models. An aspect of malocclusion change may be that a cascade of tooth movements likely takes place in small increments. A single tooth may move in a small barely detectible increment because of a heavy bite between the teeth. The heavy bite may lead to this tooth moving first, which then leads to a heavy bite in a different location which may then cause another movement elsewhere, which may then lead to a heavy bite elsewhere, and so on and so forth. A prediction of such a "domino" effect can be extremely difficult because the effects of the jaw movements and musculature are not often taken into account by the visual inspection of a medical practitioner. By obtaining digital data such as a three-dimensional scan at an initial time point and allowing sufficient time to pass before taking second and/or subsequent digital data (e.g. 6 months or 1 year later), the actual results of the bite, the jaw, and the soft tissues may be evident in the arrangement of the teeth themselves. The role of any restorative dental work can also be determined.

FIG. 9 illustrates a method 900 for generating a predicted digital representation of a patient's intraoral cavity in order to determine a future condition in the patient. The method 900, as with all other methods provided herein, can be used in combination with any embodiments of the systems and devices of the present disclosure. For example, some or all of the steps of the method 400 can be performed by one or more processors of a computer system as discussed further herein.

In step 905, first digital data of the intraoral cavity is received. The first digital data can be representative of an actual state of the intraoral cavity or one or more objects thereof (e.g., teeth, gingiva, jaws, palate, tongue, airway, TMJ, etc.) at a first time point. In some embodiments, the first time point is an initial time point at which dental and orthodontic monitoring starts for the patient. In some embodiments, the initial time point occurs after the primary teeth have erupted but before permanent teeth have erupted, e.g., between the ages of 4 to 6. Obtaining scan data of the teeth at a relatively early age can facilitate detection of dental or orthodontic conditions well before such conditions can be detected using visual examination.

In step 910, second digital data of the intraoral cavity is received. The second digital data can be representative of an actual state of the intraoral cavity or one or more structures thereof at a second time point different from the first time point. The first and second time points can be different, for example, by at least 1 month, at least 2 months, at least 3 months, at least 4 months, at least 5 months, at least 6 months, at least 7 months, at least 8 months, at least 9 months, at least 10 months, at least 11 months, at least 1 year, at least 2 years, at least 5 years, or any other interval of time appropriate to generate accurate measurements and/or predictions as described herein. The second time point may be subsequent to the first time point. The second time point can occur after the permanent teeth have begun erupting, but before all of the primary teeth have been shed, e.g., between the ages of 6 to 12.

In some embodiments, for example, the first and second digital data are three-dimensional scans of the intraoral cavity and/or include data representative of the three-dimensional surface topography of the patient's dentition and/or surrounding tissues (e.g., gingiva, palates, tongue, airway). Each scan may include the upper and/or lower arches of teeth. Three-dimensional models of the teeth may be generated based on the scans as described above and herein. The scan data taken at the two or more different times can be used to estimate the future position and/or shape of intraoral objects such as the teeth, gums, bite, etc. as further described herein. Alternatively or in combination, other types of digital data besides scan data can be used, such as sub-surface data of the tooth roots, such that positioning and/or shape of non-visible intraoral objects (e.g., tooth roots, jaws, airway) can also be determined.

Optionally, digital data representative of the intraoral cavity at further time points subsequent to the second time point can be received, e.g., third digital data obtained at a third time point, fourth digital data obtained at a fourth time point, etc. Any number of digital data sets at any number of time points can be received and later analyzed as described below and herein. The digital data herein can be obtained at any combination of time points during the dental development of the patient, such as time points before, during, and/or after the development of the permanent dentition. For example, subsequent digital data can be obtained after all of the primary teeth have been shed (e.g., after age 12) and/or once the full permanent dentition is completed (e.g., after eruption of the third molars, which typically occurs between the ages of 17 to 25).

In step 915, additional data is received. In some embodiments, the additional data provides other information useful for identifying a current condition and/or predicting a future condition in the patient. For example, the additional data can include demographic information, lifestyle information, medical information, medical history, familial medical history, and/or genetic factors. The additional data can be received at one or more different time points, which may or may not be the same time points for the collection of the first and second digital data. For example, the additional data can be received at a plurality of time points during dental development and/or concurrently with the scan data. Alternatively, additional data can be received at a single time point.

In step 920, a predicted digital representation of the intraoral cavity is generated. The predicted digital representation can be a two-dimensional or three-dimensional model of a predicted future state of the intraoral cavity or one or more structures thereof at a future time point subsequent to the first and second time points. The future time point can be at least 1 month, at least 2 months, at least 3 months, at least 4 months, at least 5 months, at least 6 months, at least 7 months, at least 8 months, at least 9 months, at least 10 months, at least 11 months, at least 1 year, at least 2 years, at least 5 years, at least 10 years, at least 20 years, or any other desired length of time subsequent to the first and/or second time points. The future time point may correspond to a life event, such as when the patient turns 18, gets married, moves, retires, travels, competes, etc.

As discussed above and herein, the predicted digital representation can be generated based on the first and second digital data using various methods. For instance, in some embodiments, the digital data at the two or more time points is compared in order to generate a comparison thereof. Any number of digital data sets from any number of time points may be compared. In some embodiments, generating the comparison involves registering the first and second digital data to each other in a common coordinate system. Generating the comparison can involve measuring a characteristic of an intraoral object at the first time point (e.g., using the first digital data), measuring the characteristic of the intraoral object at the second time point (e.g., using the second digital data), and determining a change to the characteristic between the first and second time points. Optionally, the characteristic can be measured at subsequent time points using the corresponding digital data in order to determine the change to the characteristic over the subsequent time points.

A future change to the characteristic of the intraoral object can be predicted, in response to the determined change and/or a selected time interval, and used to generate the predicted digital representation. For instance, as discussed above and herein, a rate of change in the characteristic can be determined, and the rate of change can be extrapolated to a selected future time point in order to predict the characteristic of the intraoral object at the future time point. By repeating this process for a plurality of intraoral objects (e.g., each tooth in the patient's intraoral cavity), the digital representation of the intraoral cavity at the future time point can be predicted and generated.

In one exemplary embodiment, the methods herein can be applied to generate a prediction of the patient's teeth at a future time point. In some embodiments, the positioning and/or shape of the teeth at the first time point may be measured, such as from scan data at a first time point, and the positioning and/or shape of the teeth at the second time point may be measured, such as from scan data at a second time point. Optionally, the positioning and/or shape of teeth at additional time points (e.g., a third time point) can be measured, such as from scan data obtained at additional time points. In some embodiments, the positioning and/or shape of tissues surrounding the teeth can also be measured, such as the positioning and/or shape of gingiva, the tongue, palate, airway, etc.

Many changes to the teeth between the two or more time points may have occurred. For example, one or more of the teeth may have moved, one or more of the teeth may have been worn down or lost, one or more of the teeth may have been restored or replaced, and some or all of the gums surrounding the teeth may have receded or swelled. Accordingly, movement and/or shape change velocities for one or more teeth and/or surrounding tissues can be determined. A comparison between the teeth and/or surrounding tissues at the different time points may be performed by determining the movement and/or shape changes of one or more teeth and/or surrounding tissues over the time interval between the first and second time points and determining the velocities of such movement or changes. For example, the upper dental arch at the first time point may be registered and compared to the upper dental arch at the second time point, and the lower dental arch at the first time point may be registered and compared to the lower dental arch at the second time point.

Each mouth of a person is unique because of the size, shape, and bite of the person. Any natural deterioration of the positions of the teeth may be patient to different rates of tooth movement and different areas where teeth are wearing down. For example, the bite for some patients may deepen as a result of the wear of the biting surface of the back teeth, leading to more heavy contacts in the front and greater crowding as a result of inward pressure placed on the front teeth as they collapse toward the tongue. In another example, the pressure of the tongue may lead to greater spacing and anterior bite opening for others, which may start at rates that may be barely perceptible initially but may magnify over time to significant changes. The velocities of such changes for each tooth can be determined from a comparison of the three-dimensional scans. Individual teeth may be identified and labeled. The differences in the X, Y, and/or Z positions of the individual tooth and/or one or more identified landmarks of the tooth between the two scans may be determined. Individual trajectories of the teeth may be calculated. The rate, magnitude, and direction of a tooth movement may be calculated as a three-dimensional vector. A rate and location of tooth shape change can also be determined. Areas which have worn down are likely to continue to be worn down, for example. In some embodiments, the determined rates, magnitudes, directions, and/or locations of the changes to the one or more teeth may be adjusted based on additional information such as from a comparison of tooth root locations or gum lines. For example, a comparison of tooth root locations at two separate time points can be extrapolated to determine the location of the root at any future time point, and this determined location of the root can be used at least in part to determine the changes to the tooth at the future time points and collisions. In another example, a comparison of gum lines at two separate time points can be extrapolated to determine the gum line at any future time point, and this determined gum line can be used to at least in part to determine the change to the tooth at the future time points. The determination and use of the velocities and trajectories for teeth changes based on the scans is further described above and herein.

Optionally, the changes to the teeth may be compared to data regarding similar changes of similar patients available from a patient database. The positioning and/or shape of the teeth at a future time point may be predicted, for example, based on the determined velocities of movement or shape changes of the teeth between the first and second time points and/or patient data (e.g., of similar movements or changes of similar patients) from the patient database. The prediction can be performed, for instance, by linearly extrapolating the position and/or shape data from the first and second time points to determine a vector and/or velocity of movement to the position and/or shape at a future time point. A third or further three-dimensional scans at third or further time points may be used to detect any non-linear changes and perform a non-linear extrapolation, as described further herein. For example, tooth movement along a curved path and/or an acceleration or a deceleration in tooth movement may be predicted.

In some embodiments, while the projected trajectory of each tooth may be determined, obstacles such as neighboring teeth may prevent the projected tooth movement from occurring fully. The teeth may be overlapped in three-dimensional geometries when the changes are rendered by a computer system, for example. Embodiments of the present disclosure may provide a tooth collision avoidance algorithm when predicting the future positioning and/or shape of the teeth, as discussed above and herein.

In some embodiments, the predicted digital representation is displayed to a user, e.g., as a three-dimensional model of the intraoral cavity at the future time point. The three-dimensional model may include one or more of projected teeth movements, projected teeth orientation changes, projected teeth shape changes, projected gum line changes, projected root location changes, projected bite position changes, projected airway changes, or projected tongue position changes, to name a few. The three-dimensional model data can be displayed in order to allow the medical professional to visualize and validate the predicted future position, size, shape, etc. of the teeth and/or other intraoral objects. These models may also be stored in a patient database for later use.

In step 925, a future condition of the intraoral cavity is determined. As discussed above and herein, the future condition can be an undesirable dental or orthodontic condition that is predicted to occur at the future time point if the intraoral cavity is left untreated. In some embodiments, the future conditions is determined prior to the occurrence of the future condition. Alternatively, the future condition may be determined after the future condition has occurred but before it is visually detectable. In some embodiments, the condition can be predicted based on predicted digital representation, e.g., by measuring one or more parameters of the representation to determine whether there are abnormalities present. Additional information such as the age of the patient or patient, dental developmental age, molar relationship, incisor crowding and/or spacing, arch form, facial type, airway, and overbite horizontal/vertical, to name a few, may be taken into account to predict the dental or orthodontic condition.

The computer system may automatically predict the dental or orthodontic condition or automatically provide a listing of dental or orthodontic conditions that may be applicable, for example, if the current patient or patient data falls into the appropriate ranges for a dental or orthodontic treatment, if the current patient or patient data closely matches that of a previously identified dental or orthodontic condition in the database, if the current patient or patient data closely matches that for the current patient or patient in the case of a relapsing condition. A medical professional using the computer system may then choose one or more of the conditions from the list. Alternatively or in combination, the computer system may provide and display key parameters (e.g., measurements) which the medical professional may evaluate to make a diagnosis of the dental or orthodontic condition. Optionally, the medical professional can select certain key parameters for monitoring, and the computer system can generate an alert if issues or abnormalities with those parameters are detected during the prediction process. The dental or orthodontic condition predicted, as well as treatments for the condition, may comprise any of the conditions and corresponding treatments described above and herein. In some embodiments, the methods described herein can also be applied to identify existing dental or orthodontic conditions. Further methods to identify or predict a dental or orthodontic condition and treat the condition are described in U.S. Provisional Application No. 62/079, 451, which is incorporated herein by reference.

In some embodiments, step 925 involves the automatic establishment and/or detection of reference data and/or features on the predicted digital representation. Such reference data and/or features may be used to obtain various dental measurements automatically calculated to facilitate diagnosis and treatment. Such selected reference data and features may be suitably recognized through databases, libraries and other like memory applications that comprise reference data and dental features characteristics that may enable the automatic recognition of such reference data and features through computer-implemented methods. For example, in some embodiments, the automatic establishment and/or detection of reference data and/or features may comprise the automatic establishment of reference objects, the automatic establishment of reference frames, the automatic detection of anatomical dental features, and/or the automatic construction of orthodontic references. Any of one or more of these such features, frames and references may then be used to automatically calculate suitable measurements for predicting a future condition.

In some embodiments, the automatic computation of dental measurements may comprise the computation of numerous teeth dimensions, e.g., size, shape and other tooth characteristics, as well as the computation of arch dimensions and the like, e.g., the relative position of the teeth in the arch. For example, the automatic computation of dental measurements may comprise the computation of the angular relative position, such as crown angulation (tip), crown inclination (torque) and/or crown rotation (around the tooth axis). In addition, the automatic computation of dental measurements may comprise the computation of the translational relative position of each tooth with respect to the other teeth, such as the crown level and/or crown prominence. The automatic computation of dental measurements may also comprise the computation of the relative overlap, e.g., the local overcrowding or how the teeth obstruct each other. Another computational dental measurement may comprise the relative coherence that is a derivative of the angular relative position and translational relative position measurements. For example, the relative coherence of two adjacent teeth is a difference of their relative positions with respect to the angular and translational components.

In some embodiments, the computational dental measurement includes tooth shape characteristics such as crown shapes, the mesial to distal width, the buccal to lingual width, the crown height (length of the crown in the direction of normal to the occlusal plane) and other like tooth characteristics, such as the spline curve at around crown base (spline curve on the boundary of crown and gingival surface). The automatic computation of dental measurements may also comprise the computation of various other dental features such incisor, canine, pre-molar and molar characteristics, including point features (described by center point and region around the center point, for example a cusp) and/or elongated features (described by center curve and region around the center curve, for example, groove and ridge). The automatic computation of dental measurements may comprise the computation of teeth dimensions and/or arch dimensions and the like based on one or more of the static or dynamic dental features, reference objects and/or frames established, detected and/or constructed.

In some embodiments, the automatic computation of dental measurements may further include the determination of dental alignment characteristics such as incisor ridge alignment angle, mandibular posterior alignment characteristic, maxillary posterior alignment characteristic, posterior marginal ridge relative height, buccolingual inclination distance of posterior tooth, and/or interproximal contacts. Moreover, the automatic computation of dental measurements may comprise the automatic computation of bite characteristics including, for example, occlusal contacts and occlusal relationship along the arch.

The dental measurements described herein can be used to detect the presence of undesirable dental or orthodontic conditions. In some embodiments, the extent and amount of malocclusions such as crowding, spacing, overjet, open bite, cross bite, angle classes, occlusal contact and/or the like may be automatically determined from the various dental measurements computed and then suitably displayed to a user to facilitate dental treatment and planning, as discussed above and herein. For example, overjet may be determined by the distance from the intersection point of a curve through the midpoints of mandibular incisal ridges with the middle plane on mandibular arch, to buccal surfaces of the maxillary incisors (in closed positions). As another example, overbite may be defined as a percentage of buccal surfaces of maxillary incisors that are above the curve through the midpoints of mandibular incisal ridges. In this manner, automatic determination of malocclusions may be achieved accurately, reliably and/or efficiently.

In some embodiments, the measurements may be used to automatically compute orthodontic or dental indices, such as for the evaluation and assessment of predicted future conditions. For example, the automatic computation of orthodontic or dental indices such as Peer Assessment Ratings (PAR) indices, ABO discrepancy indices, ABO objective grading systems, and the like may also be realized based on the measurement results that are automatically computed. The automated methods provide herein may reduce or eliminate errors, inaccuracies, and time-delays associated with manual calculation or visual assessment of such indices. In some embodiments, a PAR index is automatically computed by determination and assessment of measurements, such as finding anterior teeth contact points, determining posterior bite classes, detecting or measuring posterior open bite or cross bite, calculating anterior overjet and/or measuring midline discrepancies. Such indices can be computed to allow a user to efficiently assess the complexity of a case and/or measure the quality of treatment outcome during any stage of the treatment process. In addition, the use of such indices may allow treatment cases to be scored or evaluated before, during and/or after treatment.

In step 930, treatment options for the future condition are generated and/or displayed. For instance, a list of recommended treatment products and/or procedures can be generated and displayed, e.g., to a medical professional. The treatment products and/or procedures generated may be customized to the particular patient, e.g., based on the severity of the condition, patient-specific characteristics (e.g., demographic information, lifestyle information, etc.), desired parameters for treatment cost and duration, and the like. The medical professional can select one or more of the displayed treatment products and/or procedures to be used to treat the predicted dental or orthodontic condition.

The recommended treatment products and/or procedures can be generated based on the severity of the condition or predicted condition. In some embodiments, the severity of the condition or predicted condition is assessed to determine whether correction is needed. For example, correction can be recommended if the severity exceeds a threshold value (e.g., an amount of distance, rotation, arch, overbite, underbite, crowding, space, gingival gap, etc.). The threshold value can vary depending on the preferences and judgment of the medical professional. Optionally, the severity of the patient's condition or predicted condition can be displayed to the medical professional, with or without the corresponding threshold values, in order to allow the medical professional to determine whether correction is needed. If the medical professional determines that correction is needed, the list of recommended products and/or procedures can be generated and displayed as described herein. If the medical professional determines that correction is not needed, steps 935 and 945 can be omitted. In other embodiments, recommended treatment products and/or procedures can be generated if a condition or predicted condition is identified, regardless of the severity. For example, it can be advantageous to prescribe treatment when the condition is first detected, e.g., providing a bite plate at the first sign of tooth wear due to bruxism in order to limit TMJ issues, modifying oral hygiene habits (e.g., brushing habits, tooth brush type, use of mouthwash) if gingivitis is predicted, and so on.

In step 935, a predicted outcome for a treatment option is generated and/or displayed. Various methods can be used to predict the outcome of administering a treatment option to the patient. In some embodiments, the extrapolation techniques presented herein can also be used to predict the results of treatment. For instance, tooth position changes elicited by a tooth repositioning appliance can be extrapolated to a future time point in order to predict a future arrangement of the patient's teeth after wearing the appliance. Alternatively or in combination, data mining of historical patient information can be used to predict treatment outcomes. For example, data mining can be used to retrieve historical data of comparable patients (e.g., comparable with respect to type of condition, severity of condition, demographic information, lifestyle information, medical information, medical history, familial medical history, genetic factors, etc.) from patient databases, as well as historical data of comparable treatments from treatment databases. The historical patient and/or treatment data can then be used as a basis for predicting how the patient will respond to the proposed course of treatment, as well as the effectiveness, cost, and duration of such treatment.

Predicted outcomes for different treatment products and/or procedures can be compared to each other in order to facilitate selection of an optimal course of treatment (e.g., with respect to treatment effectiveness, duration, cost, patient preference, aesthetics, etc.). For instance, a two-dimensional or three-dimensional model of the intraoral cavity may be generated with the application of the treatment product(s) and/or procedure(s) taken into account. In some embodiments, a plurality of different models representing the outcomes of different treatment options are displayed and compared. Optionally, the medical professional and/or patient may be shown a model of the intraoral cavity at the future time point left untreated, as well as a similar model with the treatment as a point of comparison.

In step 940, a treatment option for the future condition is selected and ordered. The treatment option can be ordered from a treatment provider or product manufacturer. In embodiments where the selected option is a treatment product (e.g., an appliance, prosthesis, etc.), the ordering procedure can involve using patient-specific data to design and/or generate the treatment product. In some embodiments, the patient-specific data includes the digital data and/or additional data obtained in steps 905-915. For example, three-dimensional digital data representing the patient's current tooth arrangement can be used to design a shell aligner for repositioning the patient's teeth. As another example, a digital representation of the patient's teeth and jaws can be used as a basis for producing a mandibular advancement appliance for treating the patient's sleep apnea. The patient-specific data can be transmitted to a fabrication machine and/or manufacturing facility for creating the product, for instance.

It will be appreciated that the method 900 is described above as an example. One or more of the steps of the method 900 may include one or more sub-steps. The method 900 may comprise further steps or sub-steps, may omit one or more steps or sub-steps, and/or may repeat one or more steps or sub-steps. For example, three or more sets of digital data may be taken and analyzed instead of two; and, non-linear trajectories and magnitudes of teeth and/or gum movement or other changes may be determined and analyzed. In some embodiments, one or more of steps 915, 930, 935, or 940 are optional. The steps of the method 900 can be performed in any order, e.g., the order of the steps 920-905 can be varied as desired. One or more of the steps of the method 900 may be performed with a computer system as described below and herein.

Figure 10A:
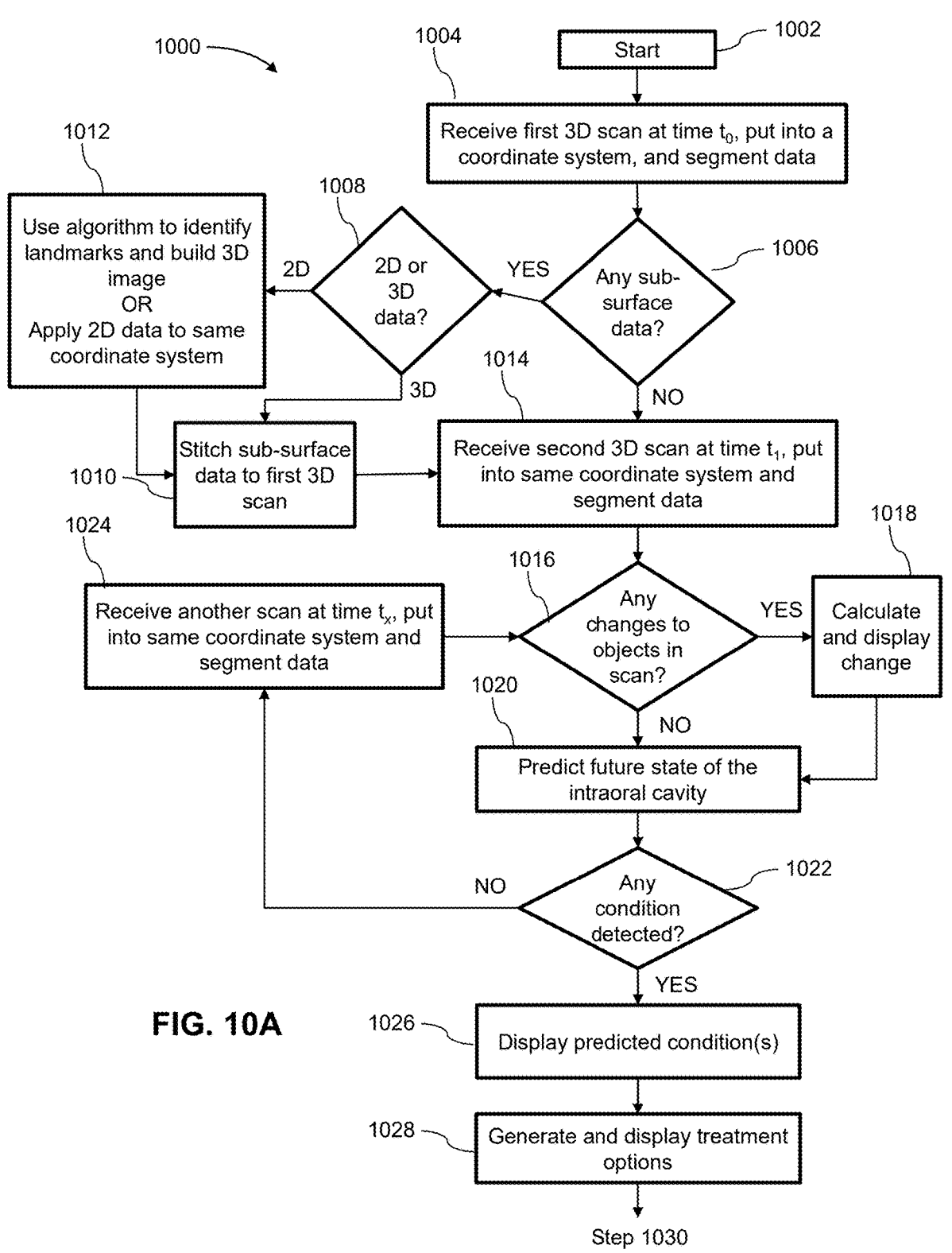
FIG. 10A shows an algorithm for predicting and treating a future condition in a patient, according to various embodiments.
Figure 10B:
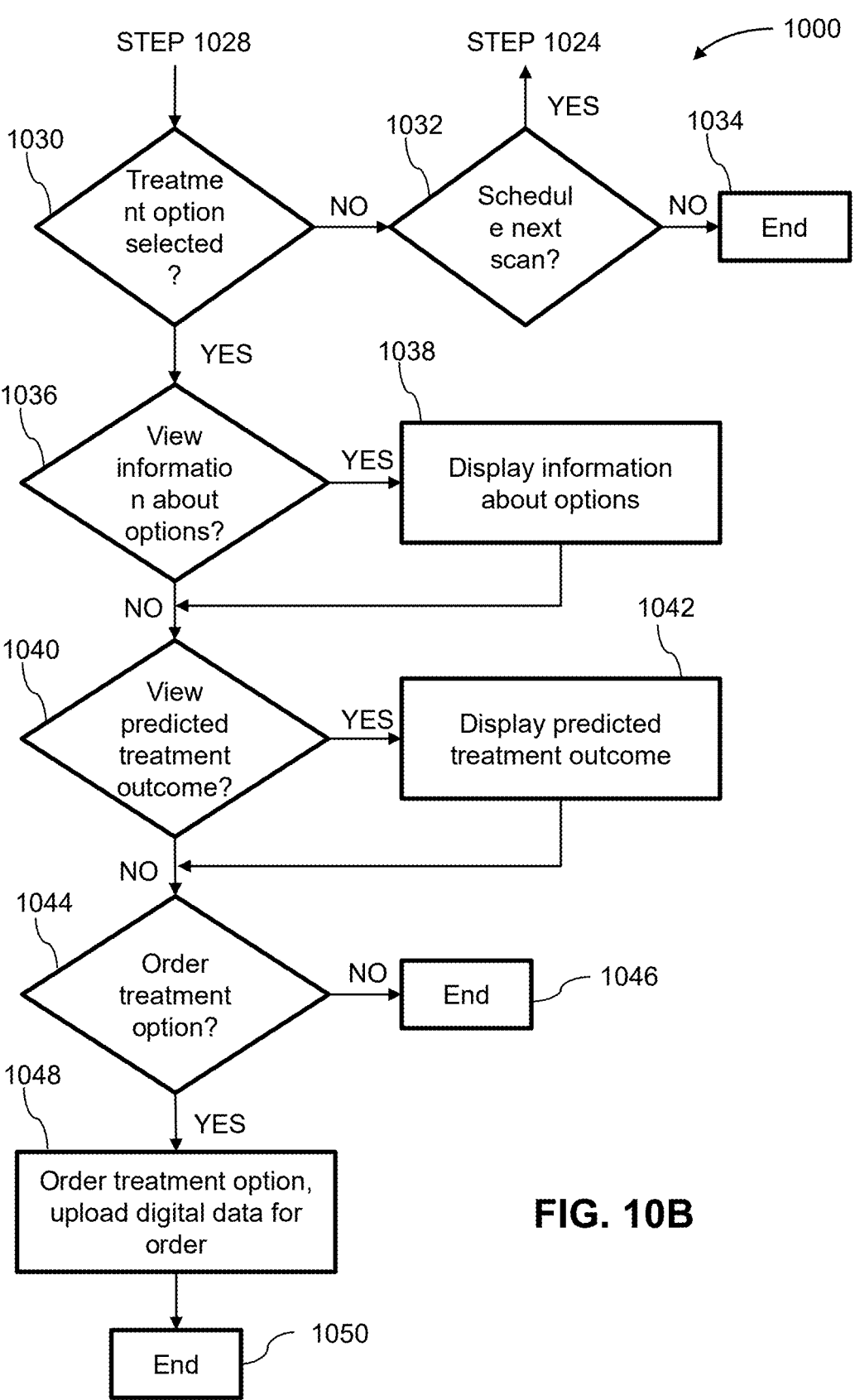
FIG. 10B is a continuation of the algorithm of FIG. 10A, according to various embodiments.

FIGS. 10A and 10B illustrate an algorithm 1000 for predicting and treating a future condition in a patient. The algorithm 1000 can be used in combination with any embodiment of the systems, methods, and devices described herein. Additionally, although the algorithm 1000 is discussed herein in the context of three-dimensional scanning, it shall be appreciated that the algorithm 1000 can also be applied to other types of digital data of the patient's intraoral cavity, such as two-dimensional image data.

The algorithm starts at step 1002. In step 1004, a first three-dimensional scan is received at a first time point (t₀) and put into a coordinate system. The three-dimensional scan can be segmented to isolate the intraoral objects of interest (e.g., individual teeth) to facilitate measurements and analysis of the objects. The scan can be processed in order to identify characteristics associated with one or more intraoral objects and/or landmarks within the intraoral cavity (e.g., gingival line, jaw width, occlusal surfaces of teeth, opposing jaw, etc.) that can be used as a basis for comparison with other scans, as discussed above and herein.

In some embodiments, the three-dimensional scan provides surface data of the intraoral cavity, such as data of the tooth crowns and gingiva. Optionally, in step 1006, the algorithm checks if any sub-surface data was received, such as data of the tooth roots. If sub-surface data was received, the algorithm determines whether the data is two-dimensional or three-dimensional in step 1008. Three-dimensional sub-surface data can be directly stitched to the three-dimensional scan, as depicted in step 1010. Two-dimensional sub-surface data may undergo additional processing before being combined with the three-dimensional scan data, as depicted in step 1012. For instance, algorithms such as surface matching algorithms can be used to identify landmarks in the two-dimensional data that can be used to build a three-dimensional image. Alternatively, the two-dimensional data can be applied to the same coordinate system as the first three-dimensional scan. The sub-surface data can then be combined with the three-dimensional scan data in step 1010.

In step 1014, second three-dimensional scan at a second time point (t₁) is received. The second scan can be placed into the same coordinate system as the first scan, segmented, and processed to identify characteristics and/or landmarks, similar to step 1004 discussed above. Optionally, sub-surface data can be obtained and stitched to the second three-dimensional scan data, similar to the process described herein with respect to steps 1006 through 1010.

In step 1016, the algorithm detects whether there are any changes to the intraoral objects depicted in the scan. Changes can be detected by comparing the first three-dimensional scan and second three-dimensional scan to each other. Detection of changes between the scan data can be performed in accordance with the various methods described herein. For instance, changes between corresponding characteristics and/or landmarks of one or more intraoral objects between the two scans can be calculated. If changes are detected, the algorithm calculates and displays the changes (e.g., on a graphical user interface), as depicted in step 1018.

If no changes are detected, the algorithm generates a prediction of the future state of the intraoral cavity, as depicted in step 1020. As discussed above and herein, step 1020 can involve generating a predicted digital representation of the intraoral cavity at a future time point subsequent to the time points $t_0$, $t_1$. The prediction can be generated based on the changes to the one or more intraoral objects determined in step 1016, e.g., using linear and/or non-linear extrapolation techniques.

In step 1022, the algorithm assesses whether any dental or orthodontic conditions were detected in the predicted future state of the intraoral cavity. If no conditions were detected, the algorithm proceeds to step 1024, where scan data at a subsequent time point $(t_x)$ is received, placed into the coordinate system, segmented, and/or processed to determine characteristics and/or landmarks. Optionally, sub-surface data can be obtained and stitched to the additional three-dimensional scan data, similar to the process described herein with respect to steps 1006 through 1010. The algorithm can then proceed to perform steps 1016 through 1022 in order to determine whether there are any changes between the new and previous scans, predict a future intraoral cavity state, and detect whether any conditions are present in the future state. The steps 1016 through 1024 can be repeated as desired in order to update the prediction as new scans are obtained. For instance, three or more scans can be compared in order to perform non-linear extrapolation of detected changes, as discussed above and herein.

If a predicted dental or orthodontic condition is detected in step 1022, the predicted condition is displayed (e.g., as a three-dimensional model and/or listing of conditions in a user interface), as depicted in step 1026. In step 1028, potential treatment options for the predicted condition(s) are generated and displayed. In step 1030, the algorithm detects whether user input selecting one or more of the displayed treatment options has been received. If no selection was made and/or the user declines to select an option, the algorithm proceeds to step 1032, in which the user is prompted to schedule the next scan of the intraoral cavity. Additional scans can be received and processed at step 1024 discussed above. Alternatively, if no additional scans are scheduled, the algorithm ends at step 1034.

If a treatment option is selected, the user is given the option to view information about the selected treatment option in step 1036. In step 1038, the information is displayed, e.g., on a graphical user interface. The user interface can provide links to a treatment provider's website with the information, for instance.

In step 1040, the user is given the option to view the predicted outcome of the treatment option. The predicted outcome can include a predicted treatment cost, duration, result, and so on, and can be displayed in step 1042, e.g., on a graphical user interface. In some embodiments, the predicted outcome can be displayed as a two-dimensional or three-dimensional model representing of a predicted future state of the intraoral cavity if the treatment option is applied. Optionally, the user can be given the option to compare predicted outcomes of different treatment options to each other and/or to an untreated state of the intraoral cavity.

In step 1044, the user is given the option to order the treatment option. If the user chooses not the order the option, the algorithm ends at step 1046. Alternatively, the algorithm may proceed back to step 1024 to receive additional scan data and continue the prediction procedure. If the user decides to order the treatment option, the option is ordered in step 1048. Optionally, digital data relevant to the treatment option (e.g., scans of the patient's intraoral cavity) can be uploaded and/or transmitted to a treatment provider in order to facilitate generation of treatment products. The algorithm then ends at step 1050. In alternative embodiments, following administration of the treatment to the patient, additional scans can be received in step 1024 in order to continue monitoring of the patient's intraoral cavity.

FIG. 13 shows a method 1300 for calculating a change in an intraoral object of a patient's intraoral cavity in order to determine a future state of the intraoral object, according to various embodiments. The method 1300 can be used in combination with any embodiment of the systems, methods, and devices described herein. In some embodiments, the method 1300 is a computer-implemented method, such that some or all of the steps of the method 1300 are performed with aid of a computing system or device, e.g., one or more processors. For example, the method 1300 can be performed by a computer system including one or more processors and memory with instructions executable by the processors to cause the system to perform the steps described herein.

In step 1310, first digital data representative of an intraoral cavity at a first time point is received. In step 1320, second digital data representative of the intraoral cavity at a second time point is received. The steps 1310 and 1320 may be performed similarly to the steps 905 and 910 of the method 900 previously described herein. Likewise, digital data from additional time points can be received and used in the subsequent steps of the method 1300. The received digital data can include any data of the intraoral cavity, such as surface data and/or sub-surface data. The received digital data can be representative of an actual state of the intraoral cavity, e.g., the actual positions, orientations, sizes, shapes, colors, etc. of one or more intraoral objects at the particular time point, and thus can be distinguished from data representing projected, desired, or ideal states of the intraoral cavity.

In step 1330, data is processed so as to determine a change in an intraoral object of the intraoral cavity over the first and second time points. The processed data can include the first and second digital data obtained in steps 1310 and 1320, for example, as well as data from other time points and/or any other additional data that may be relevant to dental orthodontic health. The intraoral object can be any of the objects described herein, such as one or more of a tooth crown, tooth root, gingiva, airway, palate, tongue, or jaw. The change in the intraoral object can be a change in any characteristic of the object, such as position, orientation, shape, size, and/or color. For example, step 1330 can involve determining a positional change of the intraoral object between the first and second time points.

Alternatively or in combination, the data can be processed in order to determine a rate of change of the intraoral object over the first and second time points. As discussed above and herein, the rate of change can be in one or more of a position, orientation, shape, size, and/or color of the intraoral object. For example, step 1330 can involve determining a velocity (e.g., movement velocity) of the intraoral object. As another example, step 1330 can involve determining a tooth shape change velocity of a tooth and/or a gingival shape change velocity of gingiva. In some embodiments, determining the rate of change involves determining a vector indicative of the trajectory and magnitude of the change over the time points, e.g., similar to those illustrated in FIGS. 4A-D, 5A-D, 6A-D, and 7A-D.

In step 1340, it is evaluated whether the determined change in step 1330 exceeds a predetermined threshold. For example, step 1330 can involve determining a positional change of the intraoral object between the first and second time points, based on the first and second digital data, and step 1340 can involve evaluating whether the positional change exceeds a predetermined threshold. The predetermined threshold can be indicative of an undesirable dental or orthodontic condition, such that the patient may be determined to have the condition or be at risk for developing the condition at a future time point if the change exceeds the threshold. The value of the predetermined threshold can be determined in various ways, e.g., based on user preferences, patient characteristics, and/or values from dental or orthodontic literature. In some embodiments, the predetermined threshold is input by a user such as a practitioner or treating professional.

In some embodiments, if the determined change exceeds the predetermined threshold, an alert is output to a user, e.g., via a user interface shown on a display. The alert can indicate to the user that the patient has developed or is at risk of developing an undesirable dental or orthodontic condition. Optionally, in response to an evaluation that the change exceeds the predetermined threshold, a plurality of options for producing a desired dental or orthodontic outcome may be generated and displayed to a user on a user interface shown on a display. The plurality of options may be a plurality of treatment options for treating an undesirable dental or orthodontic condition that is present or predicted to occur. The displayed treatment options can also include associated pricing information, treatment time information, treatment complication information, and/or insurance reimbursement information, as described above and herein.

In alternative embodiments, other criteria can be used to evaluate the determined change, including but not limited to: whether the determined change is less than a predetermined threshold, whether the determined change is approximately equal to a predetermined value, whether the determined change falls within a predetermined range, whether the determined change lies outside a predetermined range, or combinations thereof.

In step 1350, a future state of the intraoral object is determined based on the determined change. The future state can be a future position, orientation, shape, size, color, etc. of the intraoral object. For example, in some embodiments, the step 1350 involves determining a future position of the intraoral object, and the future position is determined by determining a movement trajectory based on a movement velocity calculated in step 1340. The movement trajectory may be linear (see, e.g., FIG. 8A) or non-linear (see, e.g., FIG. 8B). Accordingly, the future position of the intraoral object can be determined by extrapolating the velocity of the intraoral object to the future time point using linear or non-linear extrapolation, as appropriate. In some embodiments, a non-linear movement trajectory is determined based on digital data from more than two time points, such as first, second, and third digital data representative of an actual state of the intraoral cavity at first, second, and third time points, respectively. The non-linear movement trajectory can involve a change in a movement direction and/or change in a movement speed of the object, for instance. Such non-linear changes can be determined and extrapolated using data from more than two time points. Additionally, data from more than two time points can be used to determine other parameters, such as force vector associated with the intraoral object over the first, second, and third time points.

Optionally, a graphical representation of the future state of the intraoral object can be displayed to a user in order to facilitate visualization and diagnosis of present or future dental or orthodontic conditions. For example, if a future position is predicted, the graphical representation can show the intraoral object in the future position in the intraoral cavity. The graphical representation can be provided as part of an interactive graphical user interface shown on a display operably coupled to a computer system, as discussed further herein.

The future state of the intraoral object can be used to determine a future undesirable dental or orthodontic condition that is predicted to occur at a future time point if the intraoral cavity is left untreated. As discussed above and herein, the future condition can be predicted prior to occurrence of the future condition so as to allow for preemptive treatment. Similar to other embodiments herein, a predicted digital representation of the intraoral cavity at a future time point is generated, based on the predicted future state of the intraoral object, and used to predict the future condition.

It will be appreciated that the method 1300 is described above as an example. One or more of the steps of the method 1300 may include one or more sub-steps. The method 1300 may comprise further steps or sub-steps, may omit one or more steps or sub-steps, and/or may repeat one or more steps or sub-steps. For example, three or more sets of digital data may be taken and analyzed instead of two. Some of the steps may be optional, such as steps 1340 and/or 1350. For instance, in some embodiments, step 1350 is omitted, such that the method 1300 does not involve predicting a future state of the intraoral object and/or intraoral cavity. In such embodiments, the evaluation of whether the change exceeds a predetermined threshold may be sufficient to indicate whether an undesirable dental or orthodontic conditions is currently present or is predicted to occur in the future.

In some embodiments, the systems, methods, and devices for predicting future dental or orthodontic conditions implement one or more user interfaces to output data to a user and/or receive user input. For instance, a computer system configured to predict a future condition in a patient can include instructions for generating a graphical user interface on a display (e.g., monitor, screen, etc.). The computer system can be operably coupled to one or more input devices (e.g., keyboard, mouse, touchscreen, joystick, etc.) for receiving input from a user so as to enable interaction with the user interface. The user interface can enable the user to visualize changes in the patient's intraoral cavity, any predicted future conditions, potential treatment options, and/or predicted outcomes of treatment options.

FIGS. 11A through 11G illustrate a user interface 1100 for predicting future conditions in a patient. The user interface 1100 can be generated by one or more processors of a computer system and displayed to a user on a display. The user interface 1100 can include one or more pull-down menus 1102 allowing the user to access various functionalities, a display window 1104 for displaying digital models of the intraoral cavity or other patient data, a timeline 1106 indicating chronological information for the displayed patient data, a list of identified and/or predicted dental or orthodontic conditions 1108, a list of potential treatment options or solutions for the conditions 1110, a button 1112 or other interactive element for displaying cost information associated with one or more treatment options, and/or a navigation dial 1114 or other interactive element for manipulating the view in the display window 1104. The user may interact with the various elements of the user interface 1100 (e.g., via clicking, keyboard input, etc.) in order to perform various operations related to prediction of future conditions.

Figure 11A:
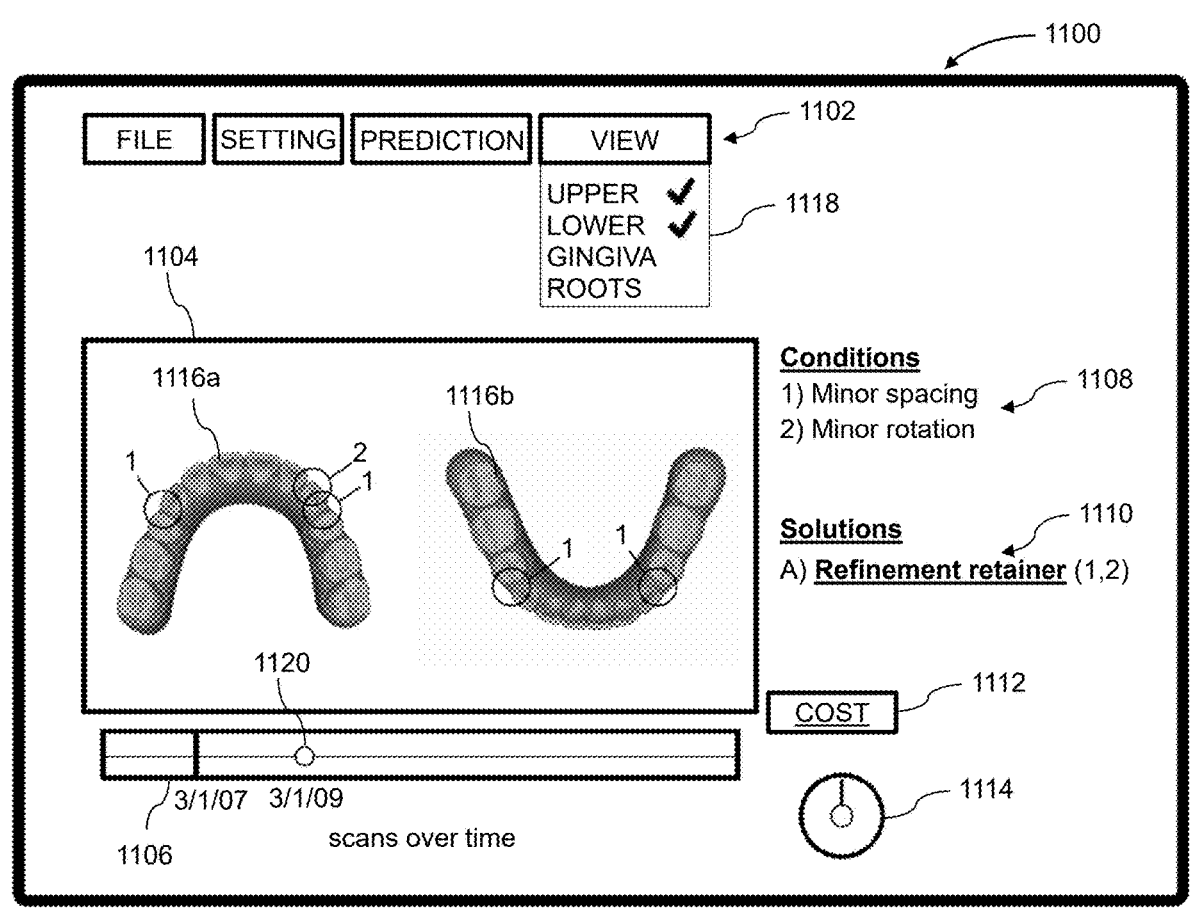
FIGS. 11A through 11G illustrate a user interface for predicting a future dental or orthodontic condition in a patient, according to various embodiments.

FIG. 11A shows the user interface 1100 displaying digital data of a patient's intraoral cavity. The digital data can be generated from any suitable combination of the digital data types described herein (e.g., scan data, sub-surface data, etc.) and can be displayed via the user interface 1100 in any suitable format. In the depicted embodiment, the digital data is displayed in the display window 1104 as a three-dimensional model of the patient's upper arch 1116*a* and lower arch 1116*b*. In alternative embodiments, the digital data can be displayed in other formats, such as two-dimensional images of the intraoral cavity. If desired, models of other portions of the intraoral cavity can also be displayed, such as models of the jaws, palate, airway, tongue, and/or TMJ. The user interface 1100 can include various types of tools and settings to allow the user to control what data is presented in the display window 1104 and how it is displayed. The user may have the option to toggle between different display formats, such as between two-dimensional and three-dimensional views, for example. In some embodiments, the user can control which portions of the intraoral cavity are displayed, e.g., by selecting the appropriate fields in the "View" option 1118 of the pull-down menu 1102. For instance, the user can choose to view the lower arch only, the upper arch only, or the lower and upper arches together (e.g., in occlusion or separately). Optionally, the user can also choose whether to view certain tissues, such as the teeth, tooth roots, gingiva, tongue, jaw, palate, airway, etc. if such data is available. Additional manipulation of the displayed data can be performed using the navigation dial 1114. For instance, the navigation dial 1114 can be used to control the position, orientation, and/or zoom level of the data displayed in the display window 1104 in three-dimensional space.

As discussed herein, digital data of the patient's intraoral cavity can be received at multiple time points. Accordingly, the user interface 1100 can be used to display and compare data from different time points. In some embodiments, the timeline 1106 displays the chronological sequence of digital data available for the particular patient, e.g., as scans over time. The user can select one or more time points using the timeline 1106 in order to display data from the selected time point(s). For instance, in the depiction of FIG. 11A, a single time point has been selected, as indicated by the marker 1120, and the digital data presented in the display window 1104 corresponds to data of the intraoral cavity obtained at the selected time point.

In some embodiments, if multiple time points are selected, the display window 1104 displays the corresponding digital data sets overlaid onto each other, thus facilitating visual comparison of data from different time points. Changes in the intraoral cavity between the different time points can be visually indicated using highlighting, coloring, shading, markings, etc., according to user preference. In some embodiments, the user interface 1100 also displays measurement data quantifying for the changes between different time points, such as dimensional, force, and/or vector data. Optionally, the user interface 1100 can display an animation of the progression of the patient's intraoral cavity over one or more selected time points. In such embodiments, the user interface 1100 can include one or more animation controls (not shown) that allow the user to play, stop, rewind, and/or fast-forward through the animation.

The user interface 1100 can display a list 1108 of existing dental or orthodontic conditions that are present in the patient's intraoral cavity at the selected time point. As discussed above and herein, the approaches presented herein can be used to identify existing conditions based on digital data of the intraoral cavity. For instance, in the depiction of FIG. 11A, minor spacing and minor rotation conditions have been identified at the selected time point. In some embodiments, the portions of the intraoral cavity that are associated with the listed conditions are identified on the data shown in the display window 1104 using visual indicators such as labels, coloring, shading, and the like. For instance, in the depicted embodiment, the affected areas of the patient's upper and lower arches 1116*a-b* have been marked with circles and labels.

In some embodiments, the user interface 1100 can display a list 1110 of potential treatment options (also referred to herein as treatment solutions) for the identified dental or orthodontic conditions. The list 1110 can indicate which condition(s) each solution is intended to treat. Optionally, the listed treatment solutions can be displayed as hyperlinks, and the user can click or select the hyperlinks in order to view additional information about each solution, such as a description, images of a treatment product or procedure, predicted cost, predicted duration of treatment, insurance and reimbursement information, treatment provider listings, treatment provider webpage, ordering information, etc. Alternatively or in combination, the predicted cost of a particular solution is displayed in response to the user selecting the "Cost" button 1114. In some embodiments, if a treatment solution is selected, the user interface 1100 displays a prediction of the treatment outcome, as discussed further herein. Optionally, the user interface 1100 can generate a display proposed timing for one or more appointments, e.g., for monitoring the progression of the detected condition(s) and/or administering the selected treatment solution.

Figure 11B:
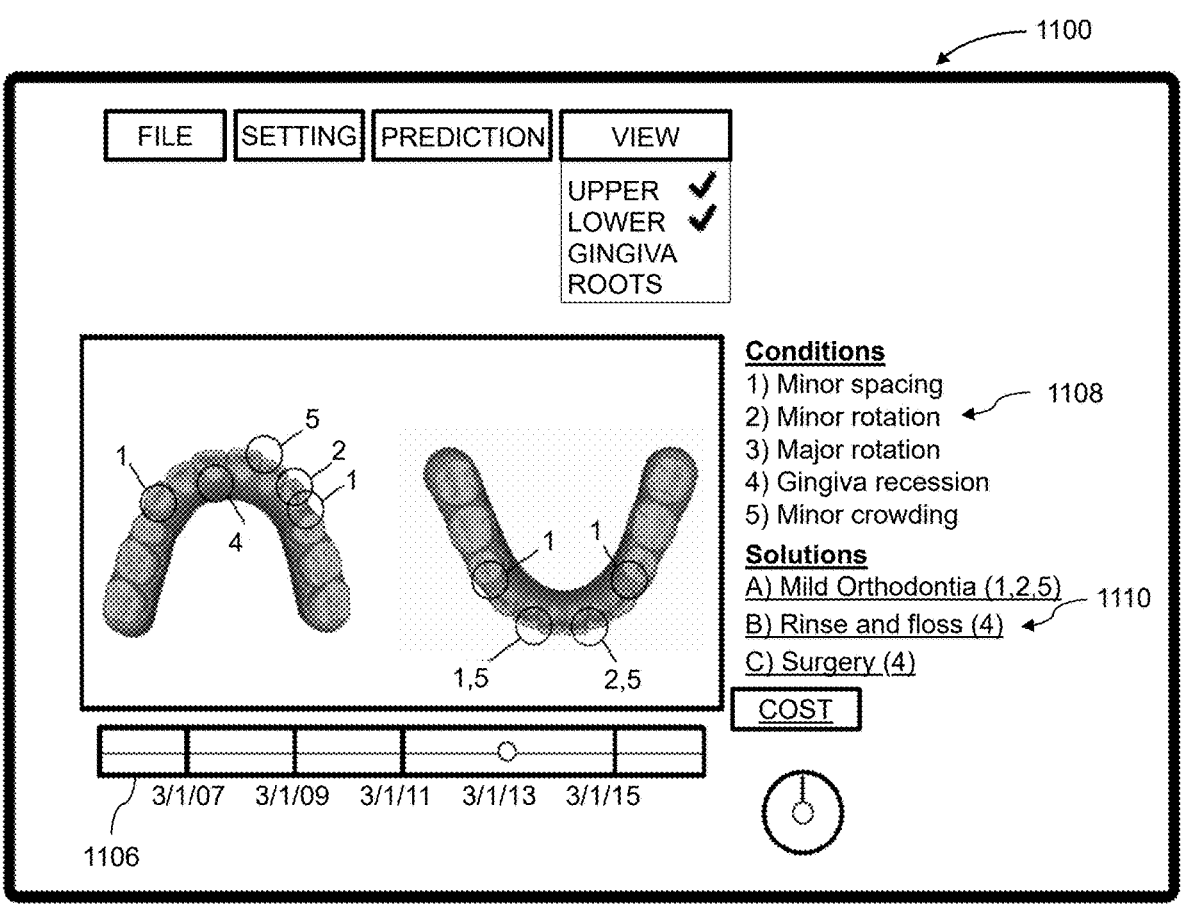

FIG. 11B shows the user interface 1100 displaying digital data obtained at additional time points. In the depicted embodiment, the timeline 1106 has been updated to include the additional time points. The lists of identified conditions 1108 and potential treatment solutions 1110 have also been updated to reflect the progression of the intraoral cavity. For instance, compared to the patient data shown in FIG. 11A, the patient data for the later time point shown in FIG. 11B indicates an increase in the number and severity of the identified conditions 1108. This is also reflected by an increase in the number and aggressiveness of the displayed treatment solutions 1110.

Figure 11C:
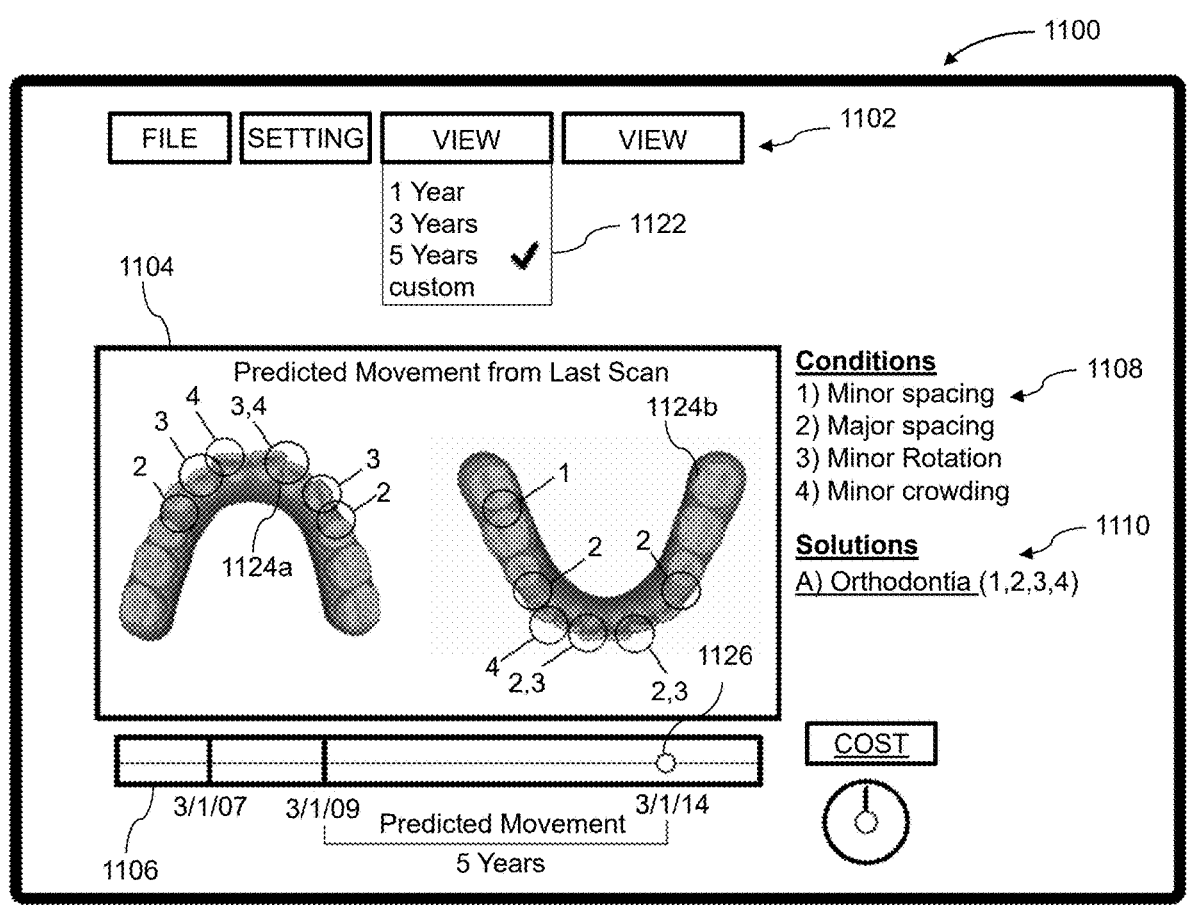

FIG. 11C shows the user interface 1100 displaying a predicted digital representation of the patient's intraoral cavity at a future time point. The predicted digital representation can generated based on digital data of the intraoral cavity from previous time points, as discussed above and herein. In some embodiments, the predicted digital representation can be generated in response to the user selecting the "Prediction" option 1122 from the pull-down menu 1102. The user can indicate the future time point for which the prediction should be generated, e.g., by selecting from one or more preset options or by entering a custom date.

Once a time interval has been selected, the predicted digital representation is generated using the digital data from previous time points, in accordance with the methods presented herein. Optionally, the user can select which time points are used to generate the prediction, e.g., by selecting the desired time points from the timeline 1106. The resultant predicted digital representation can be displayed as a two-dimensional or three-dimensional model of the intraoral cavity in the display window 1104, such as models of the patient's lower arch 1124*a* and upper arch 1124*b*. The user can adjust how the predicted representation is displayed in the display window 1104 (e.g., by adjusting position, orientation, zoom, views, etc.), as discussed herein with respect to FIG. 11A. The timeline 1106 can be updated to show the chronological relationship between the future time point represented by the prediction (e.g., as indicated by marker 1126) and the time points corresponding to the digital data used in the prediction. Additionally, the user interface 1100 can incorporate tools to allow the user to compare the predicted state of the intraoral cavity to a previous and/or current state of the intraoral cavity. For instance, the predicted digital representation can be overlaid onto the digital data from previous time points, and changes between the previous and future states can be visually indicated using highlighting, coloring, shading, markings, etc., according to user preference. Quantitative measurements for the changes can be computed and displayed, if desired. As another example, the user interface 1100 can be configured to display an animated representation of how the patient's intraoral cavity progresses from the previous time points to the future time point.

As discussed above and herein, the predicted digital representation can be used to predict one or more orthodontic or dental conditions that may occur in the intraoral cavity at the selected future time point. The predicted future conditions can be displayed to the user in the list 1108 and/or indicated on the models in the display window 1104. Additionally, potential treatment solutions for the identified conditions can be displayed in the list 1110, with links to related resources if appropriate. For instance, the prediction depicted in FIG. 11C indicates that five years from the last time point, the patient will have developed major spacing and minor crowding conditions, in addition to the minor spacing and minor rotation conditions that were already present at the last time point (see FIG. 11A). The user interface 1100 also indicates that orthodontia is a potential treatment solution for treating and/or preventing the identified conditions.

Figure 11D:
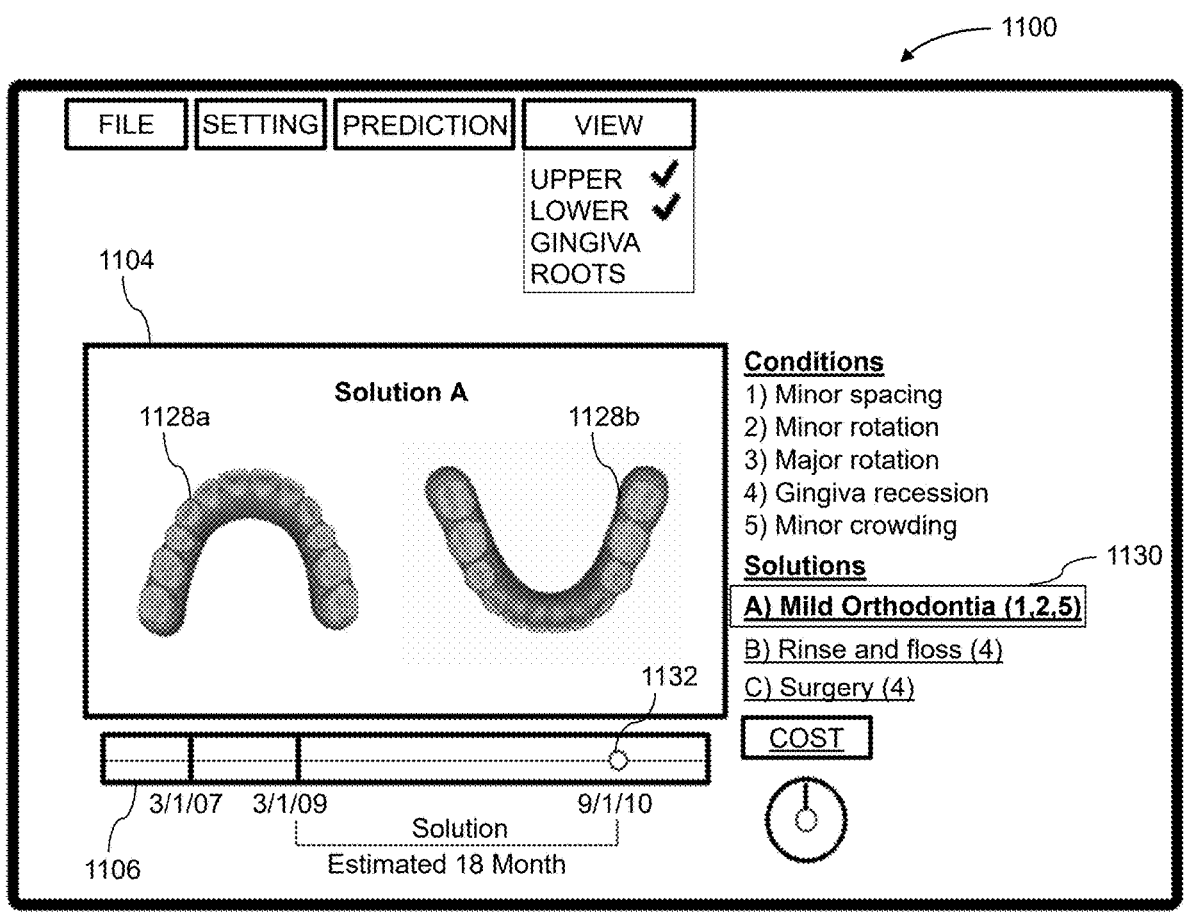

FIG. 11D shows the user interface 1100 displaying a predicted outcome of a selected treatment solution. The predicted outcome can be displayed as a two- or three-dimensional model representing the state of the intraoral cavity at a specified time point following administration of the selected solution. For instance, in the depicted embodiment, models of the patient's upper arch 1128a and lower arch 1128b are displayed in the display window 1104 and correspond to the predicted outcome of a selected treatment solution 1130 at a future time point 1132. The user can adjust how the models representing the predicted outcome are displayed in the display window 1104 (e.g., by adjusting position, orientation, zoom, views, etc.), as discussed herein. Optionally, the interface 1100 can also display other types of data related to the predicted outcome, such as predicted cost, predicted duration of treatment, insurance and reimbursement information, treatment provider listings, treatment provider webpage, ordering information, etc.

In some embodiments, the user interface 1100 allows the user to compare the predicted outcome to the previous and/or current state(s) of the intraoral cavity (e.g., by selecting the corresponding time points in the timeline 1106), as well as a predicted future state of the intraoral cavity if left untreated. For instance, the models representing the predict outcome can be overlaid onto digital data from previous time points and/or the predicted digital representation of the untreated state. Changes between the various digital models can be visually indicated, e.g., by highlighting, coloring, shading, markings, etc. Quantitative measurements for the changes can be computed and displayed, if desired.

Optionally, if multiple treatment solutions are available, the interface 1100 can include tools for comparing the characteristics (e.g., cost, duration etc.) and/or outcomes of different treatments to facilitate decision making. For instance, the interface 1100 can display multiple models of the intraoral cavity representing the outcomes of different treatment solutions (e.g., overlaid onto each other), thereby facilitating visual comparison of the efficacy of different treatments. As another example, the predicted cost, duration, and/or any other relevant parameters for each treatment solution can be displayed and compared, e.g., in list or table format.

Figure 11E:
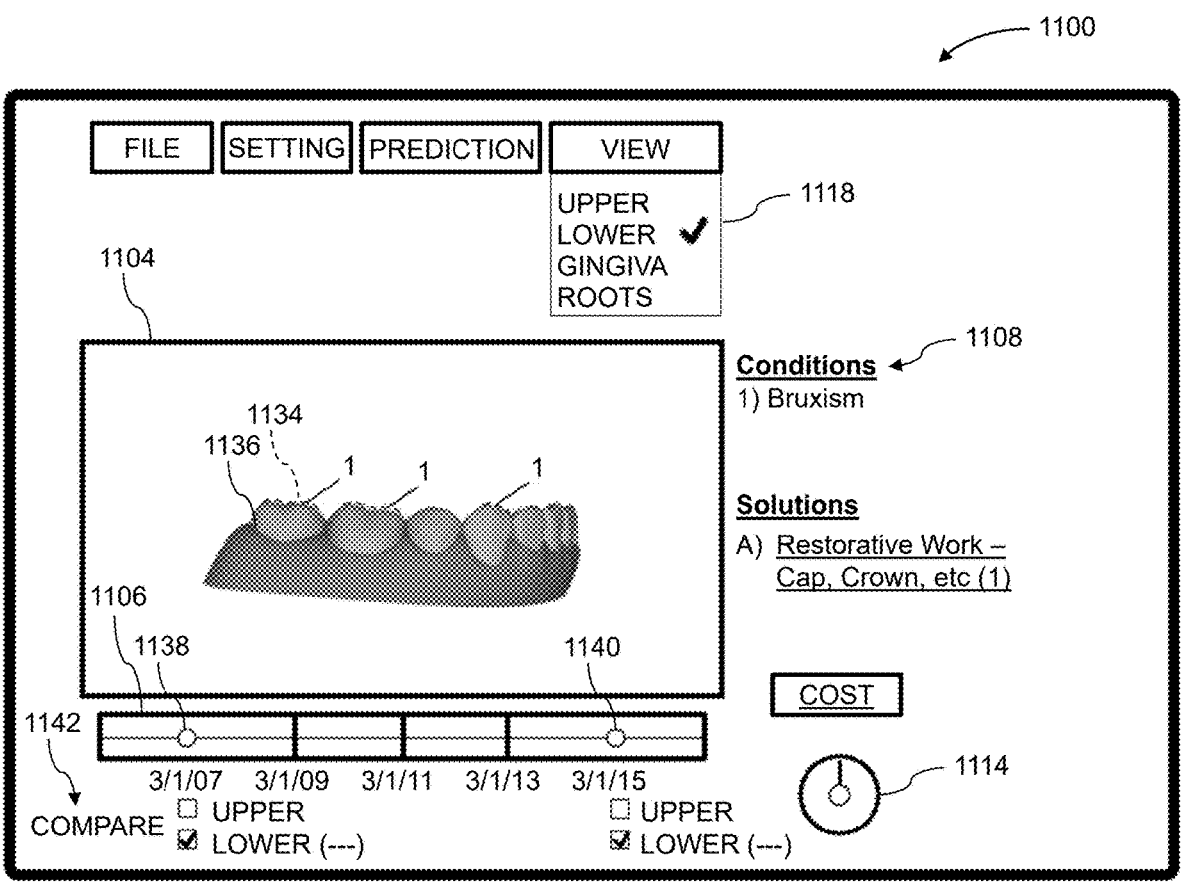

FIG. 11E shows the user interface 1100 displaying a comparison of digital data of the patient's intraoral cavity. Although the depicted embodiment illustrates a comparison of intraoral data obtained at two different time points, it shall be appreciated that the embodiments herein are equally applicable to comparisons between other types of data, such as a comparison between previously obtained intraoral data and a predicted future state of the intraoral cavity. Additionally, the approaches herein can be used to compare more than two data sets (e.g., three, four, five, or more data sets), if desired.

In some embodiments, the comparison is presented to the user in the display window 1104 as an overlay of a first model 1134 with a second model 1136. The user can select which data sets are to be compared, e.g., by making appropriate selections in the timeline 1106. In the depiction of FIG. 11E, the first model 1134 corresponds to digital data of the intraoral cavity obtained at a first time point 1138, and the second model 1136 corresponds to data obtained at a subsequent time point 1140. Similar to other embodiments herein, the user can manipulate the data shown in the display window 1104, e.g., by selecting which portions of the intraoral cavity are to be displayed in compared (e.g., via "View" option 1118 and/or display settings 1142) and/or adjusting the displayed view (e.g., via navigation dial 1114).

The different models shown in the display window 1104 can be visually distinguished from each other via coloring shading, outlining, highlighting, etc. For example, the first model 1134 is depicted with a dashed outline while the second model 1136 is depicted as a volumetric representation. Additionally, any differences or changes between the displayed models can be shown via visual indicators such as highlighting, coloring, shading, markings, labeling, etc. Optionally, if the differences or changes are indicative of an existing or predicted future condition, these can be indicated to the user in the display window 1104 and/or list of conditions 1108. For instance, in the depicted embodiment, certain teeth of the patient have been worn down between the first time point 1138 and second time point 1140, and "bruxism" is displayed in the list of conditions 1108.

Figure 11F:
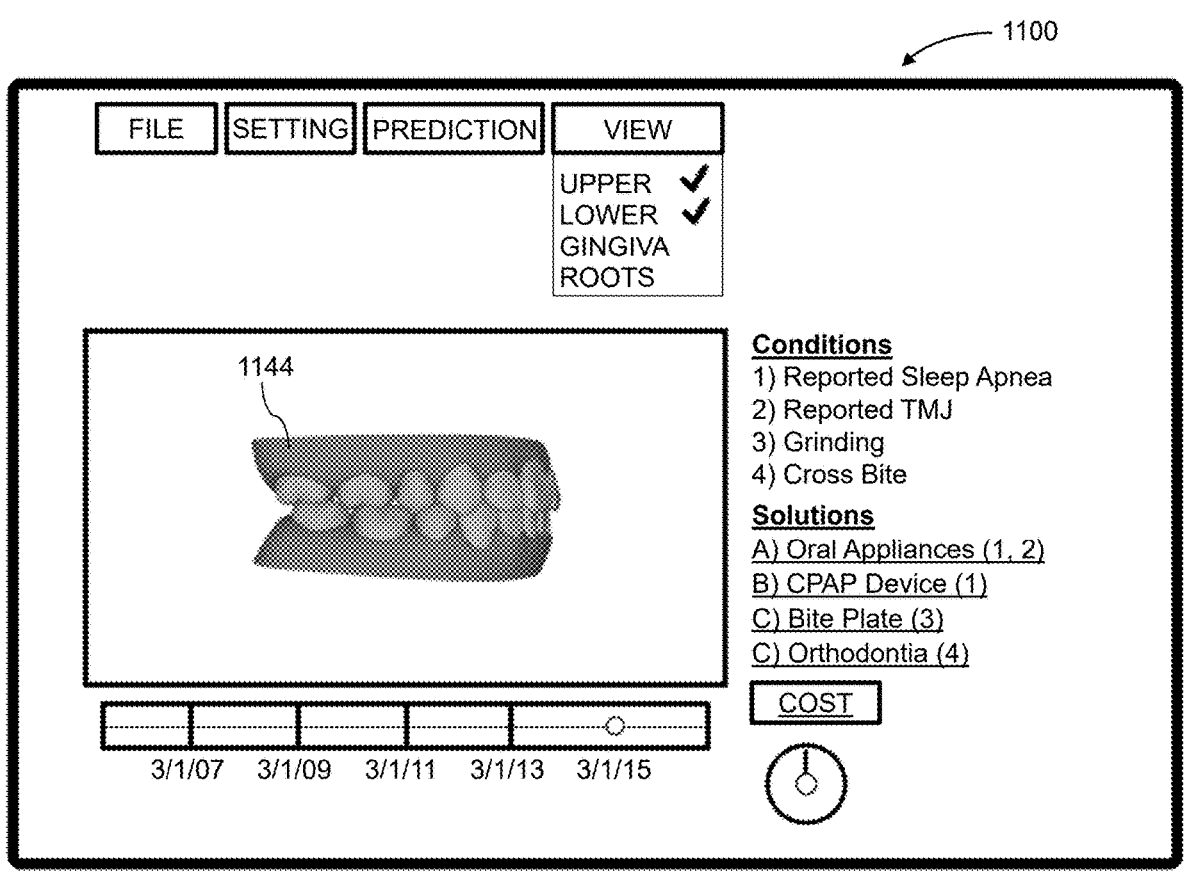

FIG. 11F shows the user interface 1100 displaying a model 1144 of the patient's arches in occlusion. As discussed above and herein, data indicative of the spatial relationship between the patient's upper and lower arches can be obtained and used to model the patient's bite. Accordingly, the user interface 1100 can be used to display the patient's arches in occlusion, alternatively to or in combination with displaying the arches separately (e.g., as depicted in FIGS. 11A through 11E). Display of the arches in occlusion can be advantageous for displaying progressions and/or predictions of bite-related conditions, such as underbite, overbite, crossbite, or similar class II or III malocclusions. Optionally, the occlusion data can be supplemented with data of other portions of the jaws in order to provide a more complete representation of the patient's intraoral anatomy, and thereby aid in the diagnosis and treatment of complex conditions involving multiple regions of the intraoral cavity. For instance, data of the TMJ and tooth roots can be displayed in conjunction with occlusion data, e.g., to facilitate visualization of root movement and bruxism issues that may contribute to TMJ pain.

Figure 11G:
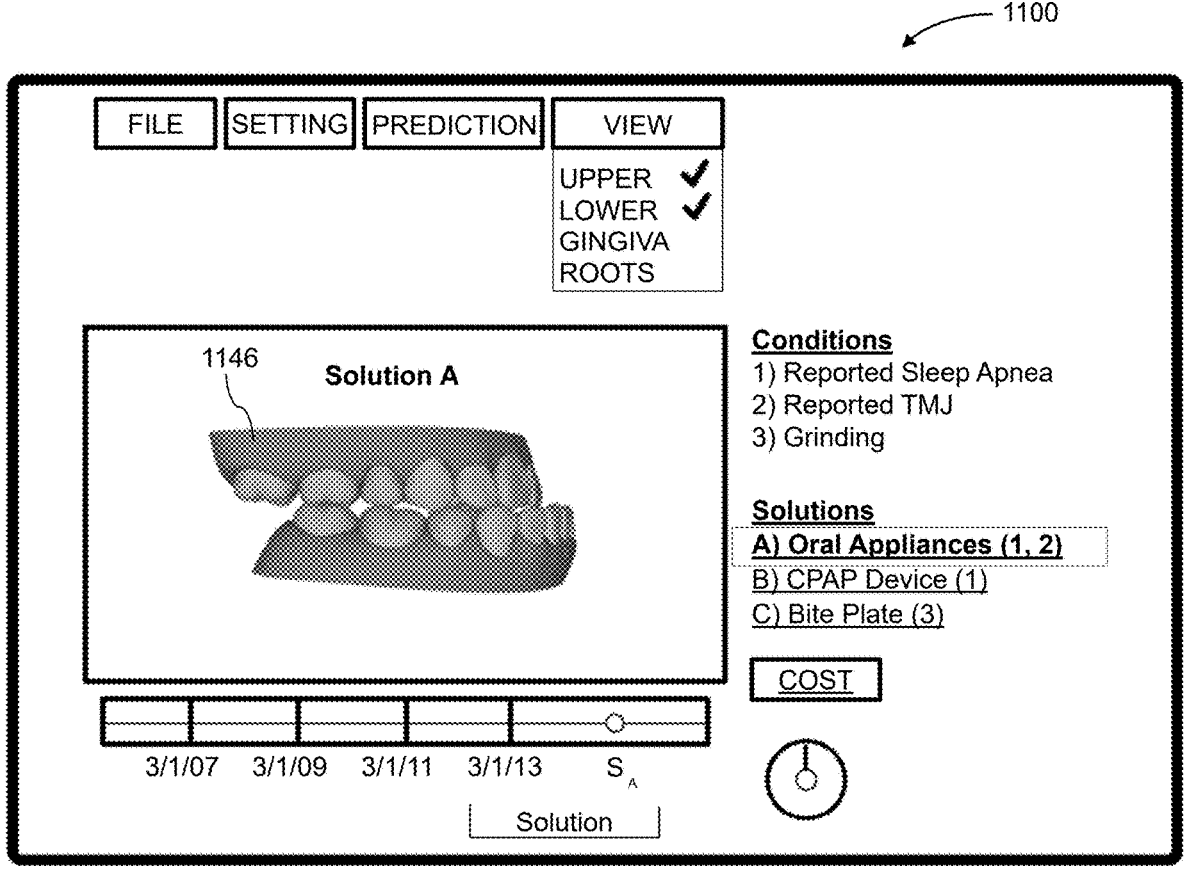

FIG. 11G shows the user interface 1100 displaying a digital model 1146 of a treatment solution for sleep apnea. In some embodiments, a treatment solution for sleep apnea involves applying an oral appliance (e.g., mandibular advancement splint) to the patient's jaws during sleep in order to advance the patient's lower jaw relative to the upper jaw. Mandibular advancement may reduce the incidence of sleep apnea events by moving the tongue away from the upper airway, for example. Accordingly, the user interface 1100 can be used to display a model 1146 representing the relative positions of the patient's jaws that would be produced by wearing the appliance. The model 1146 can be generated using digital data of the patient's intraoral cavity at a current or previous time point, such as scan data of the teeth and/or bite data indicative of the occlusal relationship between the jaws. In some embodiments, additional portions of the intraoral cavity are also displayed, such as models of the tongue, palate, and/or upper airway. Optionally, if desired, the user interface 1100 may permit the user to manipulate the model 1146 (e.g., change the positions of the upper and/or lower jaws) in order to adjust the targeted amount of jaw advancement. In some embodiments, if the user elects to order oral appliance therapy for treating the patient's sleep apnea, the model 1146 can be transmitted to a treatment provider and/or appliance manufacturer as part of the ordering process to facilitate design and fabrication of the oral appliance.

This present disclosure also provides computer systems that may be programmed or otherwise configured to implement methods provided herein.

Figure 12:
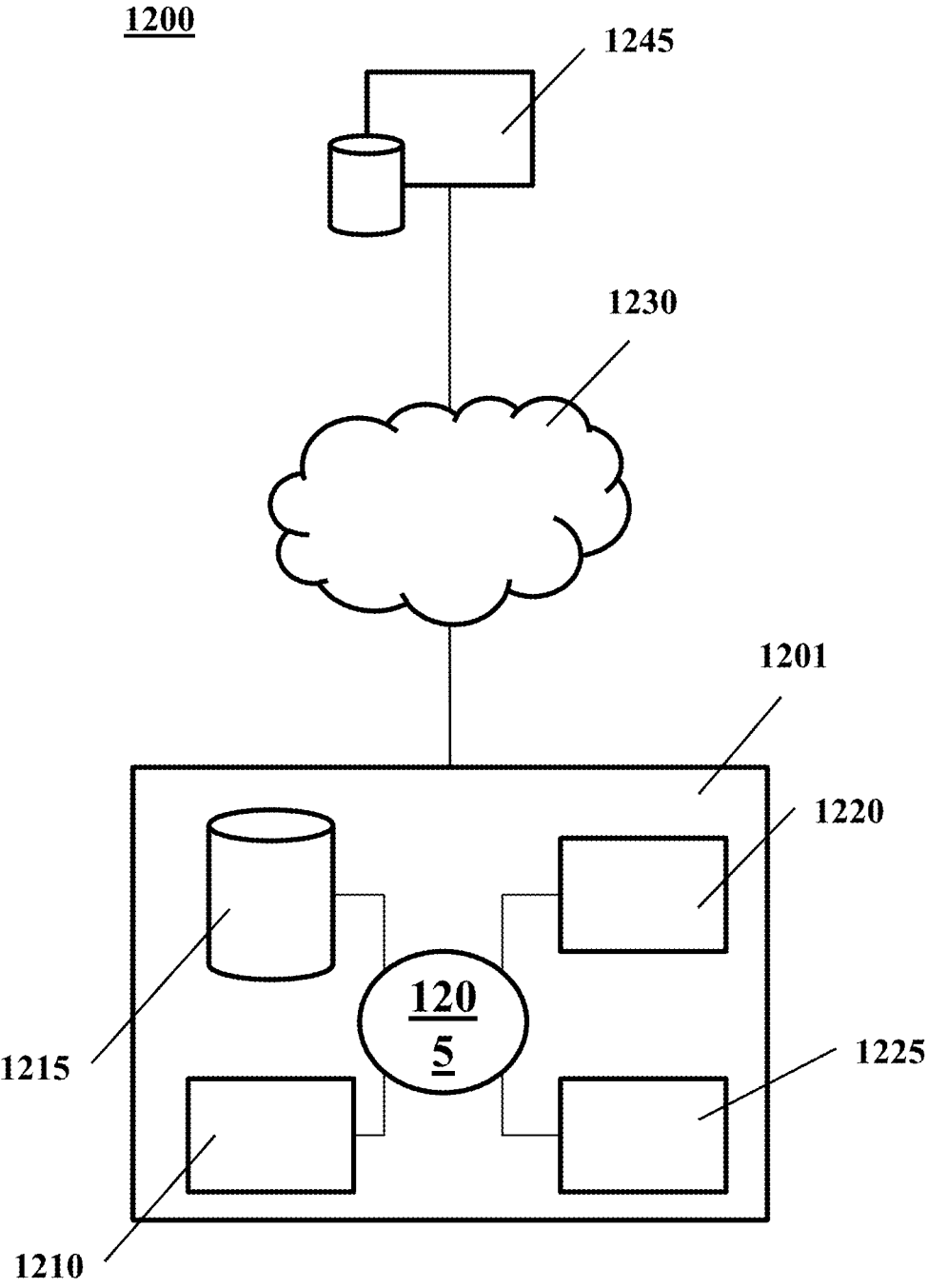
FIG. 12 shows a schematic of a system to predict a future dental or orthodontic condition in a patient, according to various embodiments.

FIG. 12 schematically illustrates a system 1200 comprising a computer server ("server") 1201 that is programmed to implement methods described herein. The server 1201 may be referred to as a "computer system." The server 1201 includes a central processing unit (CPU, also "processor" and "computer processor" herein) 1205, which can be a single core or multi core processor, or a plurality of processors for parallel processing. The server 1201 also includes memory 1210 (e.g., random-access memory, read-only memory, flash memory), electronic storage unit 1215 (e.g., hard disk), communications interface 1220 (e.g., network adapter) for communicating with one or more other systems, and peripheral devices 1225, such as cache, other memory, data storage and/or electronic display adapters. The memory 1210, storage unit 1215, interface 1220, and peripheral devices 1225 are in communication with the CPU 1205 through a communications bus (solid lines), such as a motherboard. The storage unit 1215 can be a data storage unit (or data repository) for storing data. The server 1201 is operatively coupled to a computer network ("network") 1230 with the aid of the communications interface 1220. The network 1230 can be the Internet, an internet and/or extranet, or an intranet and/or extranet that is in communication with the Internet. The network 1230 in some cases is a telecommunication and/or data network. The network 1230 can include one or more computer servers, which can enable distributed computing, such as cloud computing. The network 1230 in some cases, with the aid of the server 1201, can implement a peer-to-peer network, which may enable devices coupled to the server 1201 to behave as a client or a server. The server 1201 is in communication with an imaging device 1245, such as an intraoral scanning device or system. The server 1201 can be in communication with the imaging device 1245 through the network 1230 or, as an alternative, by direct communication with the imaging device 1245.

The storage unit 1215 can store files, such as computer readable files (e.g., 3D intraoral scan files). The server 1201 in some cases can include one or more additional data storage units that are external to the server 1201, such as located on a remote server that is in communication with the server 1201 through an intranet or the Internet.

In some situations, the system 1200 includes a single server 1201. In other situations, the system 1200 includes multiple servers in communication with one another through an intranet and/or the Internet.

Methods as described herein can be implemented by way of machine (or computer processor) executable code (or software) stored on an electronic storage location of the server 1201, such as, for example, on the memory 1210 or electronic storage unit 1215. During use, the code can be executed by the processor 1205. In some cases, the code can be retrieved from the storage unit 1215 and stored on the memory 1210 for ready access by the processor 1205. In some situations, the electronic storage unit 1215 can be precluded, and machine-executable instructions are stored on memory 1210. Alternatively, the code can be executed on a remote computer system.

The code can be pre-compiled and configured for use with a machine have a processer adapted to execute the code or can be compiled during runtime. The code can be supplied in a programming language that can be selected to enable the code to execute in a pre-compiled or as-compiled fashion.

Aspects of the systems and methods provided herein, such as the server 1201, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards, paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The server 1201 can be configured for data mining, extract, transform and load (ETL), or spidering (including Web Spidering where the system retrieves data from remote systems over a network and access an Application Programmer Interface or parses the resulting markup) operations, which may permit the system to load information from a raw data source (or mined data) into a data warehouse. The data warehouse may be configured for use with a business intelligence system (e.g., Microstrategy®, Business Objects®).

The results of methods of the disclosure can be displayed to a user on a user interface (UI), such as a graphical user interface (GUI), of an electronic device of a user, such as, for example, a healthcare provider. The UI, such as GUI, can be provided on a display of an electronic device of the user. The display can be a capacitive or resistive touch display. Such displays can be used with other systems and methods of the disclosure.

One or more processors may be programmed to perform various steps and methods as described in reference to various embodiments and implementations of the present disclosure. Embodiments of the systems of the present application may be comprised of various modules, for example, as discussed above. Each of the modules can comprise various sub-routines, procedures and macros. Each of the modules may be separately compiled and linked into a single executable program.

It will be apparent that the number of steps that are utilized for such methods are not limited to those described above. Also, the methods do not require that all the described steps are present. Although the methodology described above as discrete steps, one or more steps may be added, combined or even deleted, without departing from the intended functionality of the embodiments. The steps can be performed in a different order, for example. It will also be apparent that the method described above may be performed in a partially or substantially automated fashion.

As will be appreciated by those skilled in the art, the methods of the present disclosure may be embodied, at least in part, in software and carried out in a computer system or other data processing system. Therefore, in some exemplary embodiments, hardware may be used in combination with software instructions to implement the present disclosure. Any process descriptions, elements or blocks in the flow diagrams described herein and/or depicted in the attached figures should be understood as potentially representing modules, segments, or portions of code which include one or more executable instructions for implementing specific logical functions or elements in the process. Further, the functions described in one or more examples may be implemented in hardware, software, firmware, or any combination of the above. If implemented in software, the functions may be transmitted or stored on as one or more instructions or code on a computer-readable medium, these instructions may be executed by a hardware-based processing unit, such as one or more processors, including general purpose microprocessors, application specific integrated circuits, field programmable logic arrays, or other logic circuitry.

As used herein the term "and/or" is used as a functional word to indicate that two words or expressions are to be taken together or individually. For example, A and/or B encompasses A alone, B alone, and A and B together.

While preferred embodiments have been shown and described herein, it will be apparent to those skilled in the art that such embodiments are provided by way of example only. Numerous variations, changes, and substitutions will now occur to those skilled in the art without departing from the invention. It should be understood that various alternatives to the embodiments described herein may be employed in practicing the invention. By way of non-limiting example, it will be appreciated by those skilled in the art that particular features or characteristics described in reference to one figure or embodiment may be combined as suitable with features or characteristics described in another figure or embodiment. It is intended that the following claims define the scope of the invention and that methods and structures within the scope of these claims and their equivalents be covered thereby.

What is claimed is:

1. A method for fabricating a dental appliance based on a predicted future condition of an intraoral object in a patient's intraoral cavity, the method comprising:
receiving first digital image data representative of an intraoral cavity of the patient at a first time point;
receiving second digital image data representative of the intraoral cavity at a second time point;
evaluating a characteristic of an intraoral object of the intraoral cavity of the patient at the first time point and the second time point based on the first digital image data and the second digital image data;
predicting that a future condition of the intraoral object is expected to occur at a third time point, wherein the third time point occurs subsequent to the first time point and the second time point;
wherein the future condition is predicted based at least in part on the characteristic evaluated, wherein the future condition is predicted prior to the occurrence of the future condition, and wherein the future condition is selected from tooth crowding, tooth spacing, an overbite, an overjet, an underbite, a crossbite, an open bite, a loss of one or more teeth, or any combination thereof;
determining one or more treatment options to treat the future condition;
fabricating, using a fabrication machine, a dental appliance configured to facilitate at least one of the one or more determined treatment options.

2. The method of claim 1, wherein the characteristic of the intraoral object is one or more selected from a shape of the intraoral object, a size of the intraoral object, a color of the intraoral object, or a combination thereof.

3. The method of claim 1, wherein the evaluating the characteristic of the intraoral object comprises determining a change of characteristic of the intraoral object over the first time point and the second time point.

4. The method of claim 3, wherein the change of characteristic comprises a velocity of the change of the characteristic.

5. The method of claim 3, wherein the evaluating the characteristic of the intraoral object comprises determining a movement trajectory of the intraoral object based on the change of characteristic.

6. The method of claim 5, wherein the movement trajectory is linear.

7. The method of claim 1, wherein the future condition comprises an undesired dental or orthodontic condition that is predicted to occur at the third time point if the patient's intraoral cavity is left untreated.

8. The method of claim 1, wherein the future condition further comprises tooth collision.

9. The method of claim 1, wherein the first digital data is representative of an actual state of the intraoral cavity at the first time point.

10. The method of claim 1, wherein the second digital data is representative of an actual state of the intraoral cavity at the second time point.

11. The method of claim 1, wherein the first digital data and the second digital data comprise sub-surface data of the patient's intraoral cavity.

12. The method of claim 1, further comprising displaying a graphical representation of the intraoral object at the third time point on a user interface shown on a display.

13. The method of claim 1, further comprising:

determining a positional change of the intraoral object between the first time point and the second time point, based on the first digital data and second digital data; and evaluating whether the positional change exceeds a predetermined threshold.

14. The method of claim 13, wherein the predetermined threshold is indicative of an undesirable dental or orthodontic condition.

15. The method of claim 1, further comprising:

receiving fourth digital image data representative of the intraoral cavity at a fourth time point different from the first and the second time points; and processing the first digital image data, second digital image data, and fourth digital image data to determine a change of characteristic of the intraoral object between the first time point, the second time point, and the fourth time point.

16. The method of claim 15, further comprising:

determining a movement trajectory of the intraoral object based on a velocity of the intraoral object over the first, second, and fourth time points, wherein the movement trajectory is non-linear; and determining a future position of the intraoral object based on the non-linear movement trajectory.

17. The method of claim 16, wherein the non-linear movement trajectory comprises one or more of a change in movement direction or a change in movement speed.

18. The method of claim 15, further comprising processing the first, second, and fourth data to determine a force vector associated with the intraoral object over the first, second and fourth time points.

19. The method of claim 1, wherein predicting that the future condition of the intraoral object is expected to occur at the third time point comprises extrapolating a rate of change of the characteristic to the third time point using linear or non-linear extrapolation.

20. The method of claim 1, wherein the characteristic of the intraoral object is one or more selected from a position of the intraoral object, an orientation of the intraoral object, or both.

21. The method of claim 1, wherein the first digital data and the second digital data comprise surface data of the patient's intraoral cavity.

22. The method of claim 1, further comprising generating a display of the one or more treatment options on a display unit and receiving an input comprising selecting a treatment option of the determined one or more treatment options.

* * * * *